US006470226B1

(12) United States Patent
Olesen et al.

(10) Patent No.: US 6,470,226 B1
(45) Date of Patent: Oct. 22, 2002

(54) AUTOMATIC ELECTRODE POSITIONING APPARATUS

(75) Inventors: Soren-Peter Olesen, Klampenborg; Palle Christophersen, Ballerup; Morten Bech, Copenhagen, all of (DK)

(73) Assignee: Sophion Bioscience A/S, Ballerup (DK)

( * ) Notice: Subject to any disclaimer, the term of this patent is extended or adjusted under 35 U.S.C. 154(b) by 0 days.

(21) Appl. No.: 09/400,283

(22) Filed: Sep. 21, 1999

Related U.S. Application Data

(63) Continuation of application No. PCT/DK98/00167, filed on Apr. 29, 1998.

(30) Foreign Application Priority Data

| May 1, 1997 | (DK) | .............................................. 0496/97 |
| Aug. 1, 1997 | (DK) | .............................................. 0902/97 |
| Oct. 8, 1997 | (DK) | .............................................. 1151/97 |

(51) Int. Cl.$^7$ ............................................. G05B 19/18
(52) U.S. Cl. ...................... 700/56; 435/284; 435/287.1; 356/346
(58) Field of Search ........................... 700/56; 435/284, 435/287.1, 29; 356/346

(56) References Cited

U.S. PATENT DOCUMENTS

| 4,907,158 A | | 3/1990 | Kettler et al. |
| 4,932,044 A | | 6/1990 | Williams et al. |
| 5,108,926 A | * | 4/1992 | Klebe ........................... 435/284 |
| 5,991,028 A | * | 11/1999 | Cabib et al. ................. 356/346 |
| 6,048,722 A | * | 4/2000 | Farb et al. ................ 435/287.1 |
| 6,063,260 A | * | 5/2000 | Olesen et al. ................ 205/793 |
| 6,117,291 A | * | 9/2000 | Olesen et al. ................ 204/415 |
| 6,268,168 B1 | * | 7/2001 | Farb et al. ...................... 435/29 |

FOREIGN PATENT DOCUMENTS

| EP | 0549905 A1 | 7/1993 |
| EP | 0627358 A1 | 12/1994 |
| WO | WO 9613721 A1 | 5/1996 |

* cited by examiner

*Primary Examiner*—Thomas Black
*Assistant Examiner*—Ronald D. Hartman, Jr.
(74) *Attorney, Agent, or Firm*—Birch, Stewart, Kolasch & Birch, LLP

(57) ABSTRACT

The present invention relates to an automatic electrode position apparatus for connecting an electrode to a cell. The invention further provides methods for utilizing the apparatus of the invention. Apparatus and methods are described for studying electrical activities in cell membranes. These methods are especially useful in large scale screening programs in the pharmaceutical industry.

47 Claims, 23 Drawing Sheets

AUTOMATIC ELECTRODE POSITIONING APPARATUS

This application is a Continuation of PCT International Application No. PCT/DK98/00167 filed on Apr. 29, 1998, which designated the United States and on which priority is claimed under 35 U.S.C.§120, the entire contents of which are hereby incorporated by reference.

FIELD OF THE INVENTION

The present invention relates to an apparatus for automatically connecting an electrode to a cell. Particularly, the present invention provides an apparatus for carrying out patch clamp techniques utilized to study electrical activities, such as ion transfer channels, in biological membranes. The present invention broadly refers to a novel electrophysiology drug handling and application set up for screening chemical substances or compounds, such as high throughput, requires a low volume of solution and sample to be tested. The invention further relates to methods for utilizing the apparatus of the invention, such as in large scale screening programs in the pharmaceutical industry.

PRIOR ART

The general idea of electrically isolating a patch of membrane using a micropipette and studying the ion channels in that patch under voltage-clamp conditions was outlined by Neher, Sakmann, and Steinback in "The Extracellular Patch Clamp, A Method For Resolving Currents Through Individual Open Channels In Biological Membranes", Pflueger Arch. 375; 219–278, 1978. They found that, by pressing a pipette containing acetylcholine (ACh) against the surface of a muscle cell membrane, they could see discrete jumps in electrical current that were attributable to the opening and closing of ACh-activated ion channels. However, they were limited in their work by the fact that the resistance of the seal between the glass of the pipette and the membrane (10–50 MΩ) was very small relative to the resistance of the channel (–10 GΩ). The electrical noise resulting from such a seal is inversely related to the resistance and was large enough to obscure the currents through ion channels, the conductances of, which are smaller than that of the ACh channel. It also prohibited the clamping of the voltage in the pipette to values different from that of the bath due to the large currents through the seal that would result.

It was then discovered that by fire polishing the glass pipettes and applying gentle suction to the interior of the pipette when it made contact with the surface of the cell, seals of very high resistance (1–100 GΩ) could be obtained, which reduced the noise by an order of magnitude to levels at which most channels of biological interest can be studied and greatly extended the voltage range over which these studies could be made. This improved seal has been termed a "giga-seal", and the pipette has been termed a "patch pipette". A more detailed description of the giga-seal may be found in: O. P. Hamill, A. Marty, E. Neher, B. Sakmann & F. J. Sigworth: Improved patch-clamp techniques for high resolution current recordings from cells and cell-free membrane patches. Pflügers Arch. 391, 85–100, 1981. For their work in developing the patch clamp technique, Neher and Sakmann were awarded the 1991 Nobel Prize in Physiology and Medicine.

Ion channels are transmembrane proteins, which catalyze transport of inorganic ions across cell membranes. The ion channels participate in processes as diverse as generating and timing of action potentials, snaptic transmission, secretion of hormones, contraction of muscles, etc. Many drugs exert their specific effects via modulation of ion channels. Examples are antiepileptic compounds like phenytoin and lamotrigine, which block voltage dependent Na+-channels in the brain, antihypertensive drugs like nifedipine and diltiazem, which block voltage dependent $Ca^{2+}$-channels in smooth muscle cells, and stimulators of insulin release like glibenclamide and tolbutamnide, which block an ATP-regulated K+-channel in the pancreas. In addition to chemically induced modulation of ion-channel activity, the patch clamp technique has enabled scientists to perform manipulations with voltage dependent channels. These techniques include adjusting the polarity of the electrode in the patch pipette and altering the saline composition to moderate the free ion levels in the bath solution.

The patch clamp technique represents a major development in biology and medicine, since this technique allows measurement of ion flow through single ion channel proteins, and also allows the study of the single ion channel responses to drugs. In brief, in standard, patch clamp technique, a thin (app. 0.5–2 µm in diameter) glass pipette is used. The tip of this patch pipette is pressed against the surface of the cell membrane. The pipette tip seals tightly to the cell and isolates a few ion channel proteins in a tiny patch of membrane. The activity of these channels can be measured electrically (single channel recording) or, alternatively, the patch clamp can be ruptured allowing measurements of the channel activity of the entire cell membrane (whole cell recording).

During both single channel recording and whole-cell recording, the activity of individual channel subtypes can be characterized by imposing a "voltage clamp" across the membrane. Through the use of a feedback loop, the "voltage clamp" imposes a voltage gradient across the membrane, and thereby voltage-sensitive channels can be activated.

The time resolution and voltage control in such experiments are impressive, often in the msec or even µsec range. However, a major obstacle of the patch clamp technique as a general method in pharmacological screening has been the limited number of compounds that could be tested per day (typically no more than 1 or 2). Also, the very slow rate of solution change that can be accomplished around cells and patches may constitute a major obstacle.

A major limitation determining the throughput of the patch clamp technique is the nature of the feeding system, which leads the dissolved compound to perfused cells and patches. In usual patch clamp setups, cells are placed in large experimental chambers (0.2–2 ml), which are continuously perfused with a physiological salt solution. Compounds are then applied by changing the inlet to a valve connected to a small number of feeding bottles. However, a number of problems exist in the technique of the prior art. First, the number of different compounds is limited by the number of bottles that may be connected to the application system at one time. This number is usually less than 6. Second, the required volumes of the supporting liquid and the sample to be tested are critically high Third, the time needed to change the solute composition around cells and patches is long for usual patch clamp experiments. Fourth, the introduction and application of compounds to be tested usually involves a significant degree of manual manipulation and interruption, thus jeopardizing the integrity of the cell/pipette connection.

The development of sophisticated systems for local application of compounds to activate neurotransmitter regulated channels, like the U-tube and other systems, reduces the effective application times to 10–100 msec, which is often acceptable. However, the feeding systems which fill the U-tube are more inflexible and have lower capacity than those used for standard patch clamp. This presently limits the use of these procedures in the medical industry.

In WO 96/13721 an apparatus is disclosed for determining the effect of test samples of compounds on ion-transfer channels of a membrane, comprising an autosampler having a plurality of containers adapted to contain test samples in solution, and having means for automatically withdrawing said test samples from each of said containers and discharging them into a receptacle, a container adapted to contain a supporting liquid, a perfusion chamber adapted to receive a test sample in solution, a supporting liquid, and said membrane, said perfusion chamber comprising a reference electrode adapted to contact electrically a solution contained in said chamber, means for transporting said test samples in solution from the receptacle of said autosampler and said supporting liquid from its container into said perfusion chamber, and means for removing said test sample and said supporting liquid from said perfusion chamber, a patch pipette having an electrode therein, movably positioned over said perfusion chamber and adapted to provide a high electrical resistance seal with the surface of a patch of said membrane positioned within said chamber, and means electrically connected to said patch pipette electrode and said reference electrode for measuring the current passing through said electrodes before, during and after the introduction of said test sample into said perfusion chamber.

It is a disadvantage of the known apparatus that various manual operations are required to utilize the apparatus. For example, a new perfusion chamber with cells has to be positioned manually in the apparatus, a new pipette has to be mounted manually in the apparatus, a cell to be patch clamped is selected manually, the pipette tip is positioned manually on the membrane of the selected cell, the patch clamping is performed manually, etc.

SUMMARY OF THE INVENTION

It is an object of the present invention to provide an apparatus and a method for automatically connecting an electrode to a cell.

According to the invention, an electrode is moved towards one or more cells while an electrical parameter, such as voltage, current, resistance, conductance, inductance, capacitance, etc, is measured in an electrical circuit comprising the electrode and a chamber holding the cells. When the electrode enters nutrition liquid in the chamber holding the cells the parameter changes abruptly and also when the electrode enters a cell the parameter changes whereby contact between the electrode and the cell is detected. Upon such detection, movement of the electrode may be automatically stopped so that the electrode remains in contact with the cell membrane or, the movement may be continued a certain distance to insert the electrode in the internal part of the cell. For example, when the cell is a macroscopic cell, such as an oocyte, etc, measurements on the cell is typically performed with two electrodes inserted into the internal part of the cell.

It is a further object of the present invention to provide an apparatus and a method for automatically connecting an electrode to a cell membrane or an internal part of a cell, e.g. for recording electrical events in cell membranes of cells, that are positioned in a chamber, the apparatus and method including automation of at least one of the following steps:

positioning of a chamber with cells in an operating position, positioning of an electrode or a pipette in an operating position adjacent the chamber, selecting a cell to be connected to the electrode or pipette, e.g. to be patch clamped, moving the electrode or the pipette to the selected cell, e.g moving the pipette tip to the cell membrane of the cell to be patch clamped, patch clamping the cell, and changing solutions in the chamber and recording electrical events of the selected cell, e.g. the cell patch.

The objects of the invention are fulfilled according to the invention by an automatic electrode positioning apparatus for connecting an electrode to a cell, comprising a chamber for holding cells, an electrode movably positioned adjacent the chamber, and positioning means for holding and positioning the electrode at desired positions in relation to the chamber. The apparatus may further comprise measurement means for determination of an electrical parameter and electrically connected to the electrode and the chamber and forming an electrical circuit comprising the electrode and the chamber. A controller controls the positioning means in response to the parameter determinations so that the electrode can be automatically connected to a selected cell.

In a group of cells, specific cells may have properties that makes it desirable to connect just such cells to the electrode. Thus, the apparatus may comprise selection means for selecting a specific cell to be connected to the electrode.

For example, the selection means may comprise the measurement means and the controller, the controller being further adapted to continue to control the positioning means so that the electrode scans the chamber with cells until a cell with a parameter within a predetermined range of the parameter is detected whereby that cell is selected.

The selection means may comprise imaging means for forming an image of cells in the chamber, digitizing means for recording and digitizing the image by dividing the image into pixels, the digitizing means being in operating communication with the imaging means, and a memory for storage of the digitized image and electrically connected to the digitizing means. For example, a grey tone image may be represented digitally by a digital image comprising pixels each of which has one pixel value representing the grey tone of the corresponding pixel. Similarly, a color image may be represented by a digital image comprising pixels each of which has three pixel values, one for each of the colors red, green, and blue.

The image may be displayed on a display unit, such as a CRT monitor, etc, constituting part of a user interface means of the selection means and an operator may then select a cell to be connected to the electrode, e.g. using a mouse, specific keyboard keys, etc.

The selection means may further comprise a processor that is connected to the memory and that is adapted for determination of the position of the selected cell from its position in the image. The controller may be electrically connected to the selection means and adapted to receive the position of the selected cell and to automatically control the positioning means in response to the received position in such a way that the electrode is positioned at the determined position of the selected cell.

Alternatively, the selection of a cell may be performed automatically. For this purpose, the processor may be further adapted for processing the digitized image for identification of cells in the chamber, selection of one cell to be connected to the electrode, and determination of the position of the selected cell in the chamber.

In a preferred embodiment of the invention for automatical patch clamping of a cell, the apparatus may comprise a pipette comprising the electrode and having a pipette tip adapted to provide a high electrical resistance seal with the surface of a cell membrane. Then, the positioning means are adapted for holding and positioning the pipette at desired positions in relation to the chamber, and the controller is adapted for automatically controlling the positioning means in response to the received position in such a way that the pipette tip is positioned at the determined position of the selected cell and provides a high electrical resistance seal with the cell membrane of the selected cell whereby an electrical parameter of the cell membrane can be determined without intervention of a human operator.

Thus, according to an important aspect of the invention, an automatic patch clamp apparatus for determination of an electrical parameter of a cell membrane is provided, comprising the chamber for holding cells positioned in an operating position in the apparatus, the pipette movably positioned adjacent the chamber in its operating position and having the pipette tip adapted to provide a high electrical resistance seal with the surface of a cell membrane, the positioning means for holding and positioning the pipette at desired positions in relation to the chamber, the selection means for selecting a cell, the cell membrane of which is to be connected with a high electrical resistance seal to the pipette tip, comprising
the processor adapted for
identification of cells in the chamber,
selection of one cell to be subsequently connected to the pipette tip, and
determination of the position of the selected cell in the chamber, the controller that is electrically connected to the selection means and adapted to receive the determined position of the selected cell and to automatically control the positioning means in response to the received position in such a way that the pipette tip is positioned at the determined position of the selected cell and provides a high electrical resistance seal with the cell membrane of the selected cell, and the measurement means for determination of an electrical parameter and electrically connected to the pipette tip and the chamber and forming an electrical circuit comprising the pipette tip and the chamber whereby an electrical parameter of the cell membrane can be determined without intervention of a human operator.

The chamber is typically constituted by a well in a chamber member. The cells may be grown on a coverslip, e.g. a 3 millimetre coverslip, which is positioned in the well. Preferably, the chamber is continuously perfused with an appropriate saline solution to prevent cells from drying and dying. Below, the chamber for holding cells is also denoted the perfusion chamber or the microperfusion chamber.

A reference electrode is preferably positioned in the chamber and in contact with liquid in the chamber to facilitate recording of electrical events in a cell membrane of a cell in the chamber.

The pipette is a patch pipette which typically is a thin (app. 0.5–2 $\mu$m in diameter) glass pipette. During patch clamping of a cell membrane, the tip of the patch pipette is pressed against the surface of the cell membrane. The internal volume of the pipette may then be appropriately subjected to negative pressure for the pipette tip to seal tightly to the cell thereby forming a giga-seal between the pipette tip and the cell membrane. Preferably, the pipette has an electrode so that the activity of ion channels of the patched cell membrane can be measured electrically.

The negative pressure (suction) for the pipette tip may be generated by a modified Eppendorf oocyte injector. The injector may be modified to generate output pressures in the range from −300 hP to +300 hP in steps of 1 hP with a response time of approximately 10 msec. This fulfils patch clamping requirements.

The positioning means are adapted to receive and operationally engage with an electrode in a housing or a pipette and to move, preferably in three dimensions, the electrode or pipette to desired positions. The positioning means may comprise an electronic micromanipulator, such as a micromanipulator manufactured by Eppendorf.

The selection means may comprise any sensor suitable for detection of cells. For example, in a chamber with a very large number of cells, the electrode may be used to identify a cell by measurement of conductance between the electrode and the reference electrode of the chamber. When the electrode is lowered into the chamber, the conductance increases when it enters the liquid in the chamber and the conductance decreases again when the electrode connects to a cell membrane. A processor may be adapted for identifying cells by monitoring the conductance. In a sufficiently dense population of cells, only a small volume of the chamber need be searched by the electrode to identify a cell membrane by monitoring of the conductance and the first cell identified may be selected, e.g. for patch clamping. In this example, the position of the selected cell is known as the current position of the electrode.

The processor may comprise any computer such as a standard IBM compatible PC or a computer compatible with an Apple Macintosh (MAC).

In a chamber with a less dense population of cells, it is preferred to use an optical sensor for detection of cells and in a preferred embodiment also for selection of a cell, e.g. to be patched. Thus, the selection means may comprise imaging means, such as a microscope, etc, for forming an image of cells in the chamber and positioned adjacent the chamber, digitizing means, such as a hPCCD camera comprising a digital output, a video camera with a frame grabber, etc, for recording and digitizing the image by dividing the recorded image into pixels, each of which has a recorded intensity value, the digitizing means being in operating communication with the imaging means, a memory, such as the memory of a PC, for storage of the digitized image and electrically connected to the digitizing means.

The image may be displayed to an operator of the apparatus, e.g. on a CRT monitor, and the operator may select a cell utilizing a user interface means, such as a mouse, e.g. by moving a cursor with the mouse to a desired cell that may be selected by activation of a mouse button. The user interface means may comprise zoom means allowing selection of a specific pixel of the image of the selected cell whereby the corresponding point of the cell surface is selected to be the point of contact with the electrode or pipette.

Likewise, the operator may define the position of the tip of the electrode or pipette by moving the cursor to the corresponding position in the image. The pixel at the position of the cursor at activation of a mouse button may be selected as the position in the image of the tip of the electrode or pipette.

When the operator has selected a cell contact point to be connected with the electrode and/or to be patch clamped with the pipette, the apparatus may automatically move the electrode or pipette to the contact point, e.g. for performing automatical patch clamping.

In another embodiment of the invention, the processor is connected to the memory and further adapted for processing the digitized image for identification of cells in the chamber, selection of one cell to be subsequently connected to the pipette or electrode tip, and determination of the position of the selected cell in the chamber.

The processor may be adapted for processing the digitized image for identification of the pipette or electrode tip, and determination of the position of the pipette or electrode tip.

Any known and suitable image processing may be utilized to recognize and identify cells and/or the pipette or electrode tip, e.g. comprising edge detecting in order to identify the contour of cells and/or the pipette or electrode tip.

It is well known to represent an image digitally by dividing the image into a large number of segments, denoted pixels, and allocating digital intensity values, denoted pixel values, to each pixel. Typically, the image is divided into a matrix of rows and columns of pixels and the size of a digital image is then given by the number of pixels in a row and the number of pixels in a column. The pixel values are typically stored in an array of memory locations in a digital memory, each memory location corresponding to a pixel of the image. For example, a grey tone image may be represented digitally by a digital image comprising pixels each of which has one pixel value representing the grey tone of the pixel. Similarly, a colour image maybe represented by a digital image comprising pixels each of which has three pixel values, one for each of the calories red, green, and blue.

Further, it is well-known to process a digital image by forming a new digital image with the same number of pixels as the original image in which each of the new pixel values is generated by a linear or non-linear transformation of the corresponding original pixel value. For example, the new pixel value may be calculated from an algorithm, i.e. a spatial digital filter, of the original pixel value and pixel values of neighbouring pixel values, e.g. the new pixel value is the average of the original pixel values of the pixel in question and its eight neighbouring pixels.

It is presently preferred to identify cells utilizing spatial filtering comprising identifying original pixels and marking, e.g., a corresponding pixel of a new digital image with the same number of pixels as the original image, with a first mark when the original pixel is a pixel onto which a cell has been imaged, i.e. the pixel values of a specific number of neighbouring pixels to the original pixel in question, including the pixel in question. are lower than a selected threshold value.

The spatial filtering may further comprise identifying and marking with a second mark a group of neighbouring pixels marked with the first mark onto which a single cell is imaged by determining the number of pixels comprised in the group of neighbouring pixels and marking groups having a number of pixels within a predetermined range.

Still further, the spatial filtering may comprise identifying and marking with a third mark a group of neighbouring pixels marked with the second mark if the distance from pixels of the group of neighbouring pixels to pixels marked with the first mark is greater than a predetermined minimum distance.

The selected cell may be selected among cells that are imaged onto corresponding groups of neighbouring pixels marked with the third mark.

According to a preferred embodiment of the present invention, a set of geometrical parameters are calculated for cells with the third mark, such as maximum cell diameter, cell form factor, cell square extent, etc. The value of a selection parameter that is a function of the geometrical parameters is calculated for cells with the third mark and the selection of a cell is made based on calculated selection parameter values. For example the first cell having a calculated selection parameter value within a predetermined range may be selected or, the cell of the cells with the third mark with a selection parameter value closest to a desired value may be selected, etc. The selection parameter may be any arithmetic combination of the set of geometrical parameter, such as the product of maximum cell diameter, form factor and square extent.

The square extent of a cell is calculated by mathematically fitting a square around the cell and calculating the ratio of the number of pixels in the cell to the total number of pixels in the square. Thus, if $d_{max}$ denotes the maximum width of a cell and A the area of the cell, the square extent is given by $$\frac{A}{d_{max}^2}.$$

If the circumference of the cell is denoted C, the form factor is given by $$\frac{4\pi A}{C^2}.$$

It is seen that the form factor has a value ranging from 0 to 1 and that the form factor for a circle is 1.

A predetermined selection parameter range may be determined by manually selecting appropriate cells, e.g. with a mouse and a cursor as described above, and calculating the selection parameter value of the selected cells. Upon selection of an appropriate number of cells, e.g. 25–40, the average and standard deviation of the cells may be calculated and during selection the cell with a parameter selection value closest to the average may be selected. Thus, different types of cells may lead to corresponding different selection parameter ranges.

The position of the centre pixel of the selected cell may constitute the determined position of the selected cell.

The signal-to-noise ratio of cell images may be enhanced considerably if the cells are made fluorescent or phosphorescent, e.g. by staining the cells with a fluorescent or phosphorescent dye, by implantation of a gene for a fluorescent or phosphorescent protein, e.g. the enhanced green fluorescent protein (EGFP). Further, the imaging means may comprise optical filters for transmission of radiation emitted from the cells and blocking other radiation. This may simplify the cell selection method described above. For example, when EGFP is used, cell selection may be reduced to the steps based on the desired intensity of the green colour marking cells with the first mark, calculating selection parameter values of cells with the first mark, and selecting the cell with the best selection parameter value.

It is presently preferred that the processor is adapted to identify pixels onto which the pipette tip or electrode is imaged utilizing spatial filtering of the image.

The spatial filtering may further comprise identifying and marking with a fourth mark a pixel as a pixel onto which the pipette or electrode tip is imaged when the pixel values of a specific number of neighbouring pixels to the pixel in question, including the pixel in question, are lower than a second threshold value.

Furthermore the spatial filtering may comprise identifying a line of pixels, each pixel on the line being positioned at the centre of pixels marked with the fourth mark and being positioned on the line of the pixel in question, and the position of the pipette tip may be determined as the position of an end pixel of the line of pixels.

In order to be able to test the influence of various compounds on a cell membrane for hours without intervention of an operator, it is necessary to be able to exchange the test chamber with the cell currently patch clamped with a new test chamber and a new patch pipette so that it is ensured that the test results always can be relied upon.

Thus, preferably, the apparatus further comprises a chamber member having a plurality of chambers for holding cells, and chamber member moving means for sequentially moving the chambers from a chamber storage position to the operating position.

It is preferred that a plurality of test cell cultures are introduced into the respective chambers of the plurality of chambers before performing tests of compounds. Preferably, the cells are grown on a layer of protein on a coverslip that is positioned in a respective chamber prior to testing of compounds.

The term "operating position" means that the positioning means for holding and positioning the pipette and the chamber are positioned in relation to each other in such a way that a selected cell in the chamber can be patch clamped to the pipette tip. The chamber member with the chambers may be moved in relation to fixed, positioning means or the positioning means may be moved in relation to a fixed chamber member.

Preferably, the present apparatus comprises chamber member moving means for moving a chamber from a first storage position in which position the chamber may be supplied with a liquid, e.g. a saline solution, sustaining living cells, to the operating position, and to another storage position when a cell in another chamber is to be patched.

The chamber member moving means may comprise the positioning means as they may be adapted to push and/or pull the chamber member to desired positions.

The chamber member may comprise a chamber member memory means for storage of data and the apparatus may comprise means for reading the data contained in the chamber member memory means.

The data may comprise an expiry date of the chamber member, identification data, calibration data, etc.

In order to facilitate correct movement of a chamber from the unused storage position to the operational position, the chamber member moving means may be controlled in any known manner. This known manner may be a movement controlled by time, length of movement, angle of rotation of the motor shaft, or optical, electrical or mechanical means may be provided for determining when the desired chamber is in its operating position and for terminating the movement.

The chamber member may comprise chambers arranged in a rectangular array of columns and rows of chambers, the chamber member being moved in relation to the positioning means along axis of rows and columns when a new chamber is moved to its operating position, or, the chambers may be arranged in circular arrays, e.g. on a turn-table, the circular array being rotated in relation to the positioning means when a new chamber is moved to its operating position.

The chamber member may be mounted on a mounting plate which can be moved in an x-y plane by two electromotors and the chamber member may be rotatable, e.g. by a third motor, about an axis perpendicular to the x-y plane so that the individual chambers can be positioned in their respective operating positions by rotation of the chamber member. The imaging system may further comprise an inverted microscope forming an assembly with the mounting plate. The position of the focus plane of the microscope may be adjustable thus, facilitating autofocussing prior to initiation of pipette and cell recognition.

Holders for holding electrodes or pipettes may be positioned with the electrodes or pipettes in an array, e.g. in two rows, on a member that is positioned on the mounting plate.

Alternatively, the chamber member may further comprise holders for holding pipettes.

The positioning means may be further adapted to selectively withdraw a pipette from its holder and to insert the pipette into its holder, e.g. when the corresponding chamber is in its operating position.

The apparatus may further comprise means for supplying liquid, such as a saline solution, to the chambers of the chamber member.

Preferably, the means for supplying liquid to the chambers of the chamber member comprises means for supplying a first liquid to the chambers in a storage position and a second liquid to the chamber in the operating position.

The apparatus may further comprise suction means for removing excess liquid flowing through the chambers.

According to the present invention the patch clamp technique is combined with the use of an autosampler, a combination which was unobvious at the outset to a person skilled in the art, especially due to the fact that the technique is sensitive to disturbances, such as vibrations and electrical noise arising from the autosampler, so that it would at best have been considered an impossible or inoperative combination.

It is a further object of the present invention to provide and adapt apparatus for automatic drug handling and application, and to utilize the apparatus in an electrophysiological system for screening of chemical substances or compounds to measure their effect on ion channel transfer, the novel system providing high throughput and low fluid volume requirements.

It is yet a further object of the present invention to reduce the needed amount of any chemical compound for testing as well as to increase the rate of screening, thereby providing the first electrophysiology test system suitable for commercial pharmaceutical company screening.

It is still further an object to provide novel microperfusion chamber structures having microperfusion chambers of extremely low volume.

It is still an additional object of the invention to provide novel methods for carrying out patch clamp technique utilizing the apparatus of the present invention. The foregoing and other objects, advantages, and characterizing features of the invention will become apparent from the following description of certain illustrative embodiments thereof considered together with the accompanying drawings, wherein like reference numerals signify like elements throughout the various figures.

What we believe to be our invention, then, inter alia, comprises the following, singly or in combination:

An apparatus for determining the effect of test samples of compounds on ion-transfer channels of a membrane, comprising:
an autosampler having a plurality of containers adapted to contain test samples in solution, and having means for automatically withdrawing said test samples from each of said containers and discharging them into a receptacle,
a container adapted to contain a supporting liquid,
a perfusion chamber adapted to receive a test sample in solution, a supporting liquid, and said membrane, said perfusion chamber comprising a reference electrode adapted to contact electrically a solution contained in said chamber, means for transporting said test samples in solution from the receptacle of said autosampler and said supporting liquid from its container into said perfusion chamber, and means for removing said test sample and said supporting liquid from said perfusion chamber, a patch pipette having an electrode therein, movably positioned over said perfusion chamber and adapted to provide a high electrical resistance seal with the surface of a patch of said membrane positioned within said chamber, and means electrically connected to said patch pipette electrode and said reference electrode for measuring the current passing through said electrodes before and after the introduction of said test sample into said perfusion chamber, such apparatus wherein the means for transporting test samples and supporting liquid to said perfusion chamber includes a U-tube mounted over said perfusion chamber and having an aperture therein for releasing a test sample and its supporting liquid into said perfusion chamber; and apparatus for determining the effect of test samples of compounds on ion-transfer channels of a membrane, comprising:

an autosampler having a plurality of containers adapted to contain test samples in solution, and having means for automatically withdrawing said test samples from each of said containers and discharging them into a receptacle, a container adapted to contain a supporting liquid, a microperfusion chamber adapted to receive a test sample in solution, a supporting liquid, and said membrane, the volume of said microperfusion chamber being about 5 microliters to about 50 microliters, said microperfusion chamber comprising a reference electrode adapted to contact electrically a solution contained in said chamber, means for transporting a test sample in solution from the receptacle of said autosampler and said supporting liquid from its container into said microperfusion chamber and means for removing said test sample and said supporting liquid from said microperfusion chamber, a patch pipette having an electrode therein, movably positioned over said microperfusion chamber and adapted to provide a high electrical resistance seal with the surface of a patch of said membrane positioned within said chamber, and means electrically connected to said patch pipette electrode and said reference electrode for measuring the current passing through said electrodes before and after the introduction of a test sample into said microperfusion chamber;

such apparatus wherein the volume of said microperfusion chamber is in the range of about 10 microliters to about 15 microliters; such apparatus wherein the volume of said microperfusion chamber is in the range of about 10 microliters to about 12 microliters; such apparatus having means for aspirating waste liquid from said microperfusion chamber; such apparatus wherein said means of said autosampler for automatically withdrawing said test samples from said containers and discharging them into a receptacle comprises a syringe pump and a needle connected thereto; and such apparatus wherein a tubular coil is positioned in series with said means for transporting said test sample for quantitatively determining the volume of the sample introduced into said microperfusion chamber.

Also, a microperfusion chamber assembly comprising: a base, an aperture in said base, and transparent means over the bottom of said base. said aperture and said transparent means cooperating to define the side walls and the bottom of a microperfusion chamber, a reference electrode arranged to contact a liquid in said chamber, means for introducing a liquid into said chamber, means for aspirating liquid from said chamber, and means for electrically connecting said reference electrode to an electrical measuring device;

such a microperfusion chamber assembly wherein said transparent means forming the bottom of said chamber is a transparent coverslip; such a microperfusion chamber assembly wherein said base comprises silver having a coating of a silver halide deposited over at least the surface of the aperture defining the side walls of said microperfusion chamber, thereby providing a reference electrode in said base adapted to make electrical contact with a liquid contained in said chamber; such a microperfusion chamber assembly wherein said base comprises silver having a coating of silver chloride deposited over at least the surface of the aperture defining the side walls of said microperfusion chamber; such a microperfusion chamber assembly wherein said base comprises silver having a coating of silver chloride deposited over its entire surface including the side walls of said chamber, such a microperfusion chamber assembly wherein said microperfusion chamber is cylindrical, frustoconical, or ellipsoid; such a microperfusion chamber assembly wherein the volume of said microperfusion chamber is about 5 microliters to about 50 microliters; such a microperfusion chamber assembly wherein the volume of said microperfusion chamber is about 10 microliters to about 15 microliters; such a microperfusion chamber assembly wherein the volume of said microperfusion chamber is about 10 microliters to about 12 microliters; and a microperfusion chamber assembly comprising a base formed of a non-electrically conductive material, an aperture provided in said base, and transparent cover means at the bottom of said base, said aperture and said transparent cover means cooperating to define the side walls and bottom of a microperfusion chamber, a reference electrode mounted in said base extending through a side wall of said microperfusion chamber and arranged electrically to contact a liquid contained in said chamber, means for introducing a liquid into said chamber, means for aspirating liquid from said chamber, and means for electrically connecting said reference electrode to an electrical measuring device;

such a microperfusion chamber assembly wherein said base comprises a plastic material; such a microperfusion chamber assembly wherein said plastic material is polymethyl methacrylate, polystyrene, polyvinyl chloride, or polycarbonate; such a microperfusion chamber assembly wherein said electrode comprises a silver wire surrounded by a mixture of particulate silver and a silver halide; such a microperfusion chamber assembly wherein said electrode comprises a silver wire surrounded by a mixture of particulate silver and silver chloride; such a microperfusion chamber assembly wherein said particulate silver and silver chloride are affixed to said silver wire; such a microperfusion chamber assembly wherein said means for introducing a liquid into said microperfusion chamber is a groove provided in said base cooperating with said transparent cover means to define a channel, the proximal end of said channel communicating with said microperfusion chamber, and an aperture provided at the top of said base communicating with the distal end of said channel and adapted to have an inflow duct connected thereto for introducing a liquid into said microperfusion chamber;

such a microperfusion chamber assembly wherein the volume of said microperfusion chamber is about 5 micro-liters to about 50 microliters; such a microperfusion chamber assembly wherein the volume of said microperfusion chamber is about 10 microliters to about 15 microliters; and such a microperfusion chamber assembly wherein the volume of said microperfusion chamber is about 10 microliters to about 12 microliters.

Also, a method for determining the effect of test samples of compounds on ion-transfer channels of a membrane contained in a perfusion chamber, wherein a patch pipette having an electrode therein has its tip engaged in a gigaohm seal with the surface of said membrane, and wherein a reference electrode is provided in said chamber adapted to contact a solution contained in said chamber, comprising continuously or periodically introducing a supporting liquid containing ions, the transfer characteristics of which are to be determined as a baseline reference, into said chamber, periodically loading one of said test samples dissolved in the same supporting liquid into said chamber utilizing an autosampler having a plurality of containers holding test samples in solution, and measuring the electrical current flowing in an electrical measuring means circuit connected between said pipette electrode and said reference electrode both before and after introduction of said test sample into said perfusion chamber, and repeating the procedure; such a method wherein said supporting liquid is continuously introduced into said perfusion chamber and the excess aspirated, and wherein said autosampler is programmed periodically to introduce a test sample into the flowing stream of said supporting liquid to flow therewith into said perfusion chamber; such a method wherein said perfusion chamber is a microperfusion chamber having a volume of 5 microliters to about 50 microliters; such a method wherein the volume of said microperfusion chamber is about 10 microliters to about 15 microliters; such a method wherein the volume of said microperfusion chamber is about 10 microliters to about 12 microliters; such a method wherein said supporting liquid is periodically introduced into said perfusion chamber and the excess aspirated, and wherein said autosampler is programmed periodically to cause a test sample to flow into said perfusion chamber; such a method wherein some of said containers in said autosampler contain said supporting liquid and wherein said autosampler is programmed periodically to introduce said supporting liquid and said test sample sequentially into said perfusion chamber; such a method wherein only small volumes of both test samples and supporting liquid are employed, wherein said perfusion chamber is a microperfusion chamber having a volume of about 5 to about 50 microliters, wherein some of the containers in said autosampler contain said supporting liquid, and wherein said autosampler first aspirates a volume of supporting liquid from one of said containers and causes the supporting liquid to enter said microperfusion chamber, and wherein said autosampler subsequently aspirates a test sample from one of said containers and causes the test sample to enter said microperfusion chamber and to replace said supporting liquid in said chamber, and wherein an electrical measurement is made both when said supporting liquid and when said test sample are present in said microperfusion chamber; such a method wherein the volume of said microperfusion chamber is about 10 microliters to about 15 microliters; such a method wherein the volume of said microperfusion chamber is about 10 microliters to about 12 microliters; such a method wherein an external electrical current is imposed on said electrodes to bring the reference current to the desired value; and such a method wherein an external electrical current is imposed on said electrodes to bring the reference current to the desired value.

DESCRIPTION OF THE DRAWINGS

FIG. 24 shows a "size" filter used for spatial filtering in step 3 of the "best cell" determination method, FIG. 25 shows a "isolation" filter used for spatial filtering in step 4 of the "best cell" determination method.

DESCRIPTION OF THE PREFERRED EMBODIMENTS

The present invention provides apparatus for carrying out patch clamp techniques utilizing an autosampler such as that utilized with HPLC apparatus to provide a very rapid means for carrying out a large number of experiments in a short period of time. The invention also permits carrying out patch clamp experiments utilizing only small amounts of test sample and small amounts of supporting liquid. The present invention also provides several novel structures for microperfusion chambers capable of supporting patch clamp studies while utilizing only very small amounts of the test samples and very small amounts of supporting liquid. The present invention also provides several different procedures for carrying out patch clamp experiments utilizing the novel apparatus. Furthermore the present invention provides a method and an apparatus for automatic recognition of cells and of a pipette tip, facilitating automatic patch clamping and testing of the cells.

Figure 1:
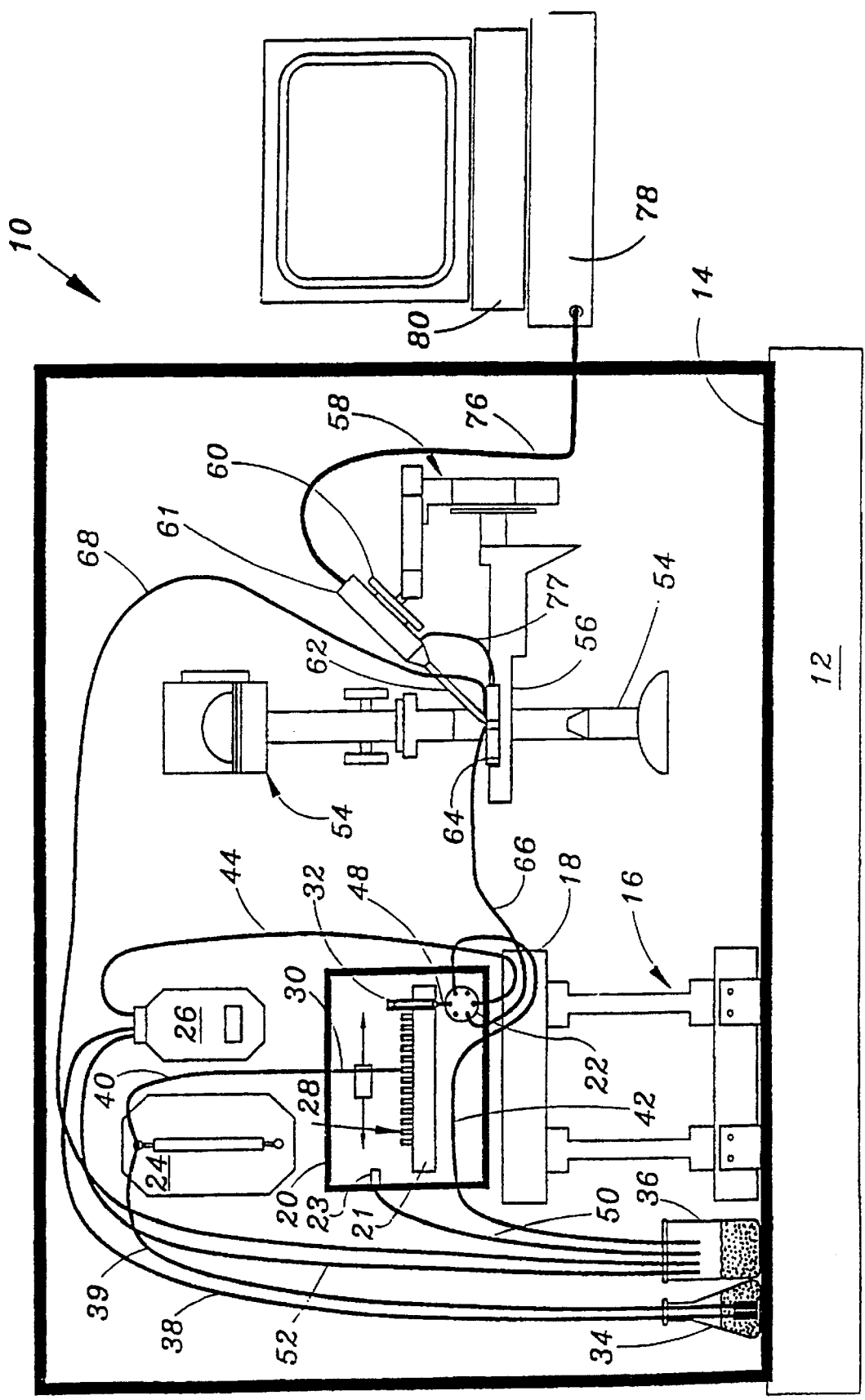
FIG. 1 is a schematic view of a general assembly of components utilized in combination in practising the several embodiments of the present invention.

Referring to FIG. 1, a general assembly of components for practising the present invention is shown. The arrangement shown is particularly designed for use in practising the embodiment of the invention termed the "continuous flow technique". However, with a few modifications the assembly may be utilized in practising other embodiments of the invention to be described. The assembly of components 10 comprises an air table 12 supporting a Faraday cage 14. Mounted within the Faraday cage 14 is a bridge 16 supporting a table top 18. An autosampler 20 (Gilson Model 231 SL), generally used with an HPLC (High Performance Liquid Chromatograph) system, and equipped with a multiple connection valve 22, is mounted on the table top 18, together with a syringe pump 24, and a peristaltic pump 26 (Gilson Model Minipuls 3). Test compounds in solution are contained in sample containers 28, arranged in an autosampler tray 21. A needle 30, a component of the autosampler 20, is mounted to be movable both laterally and vertically among the containers 28. A rinsing station 23 is provided to collect solution used 25 in rinsing the needle 30. An injection port 32 communicates with the multiple connection valve 22. The syringe pump 24 is connected to the needle 30 by a duct 40 and, when in operation, causes the needle 30 to draw up a measured volume of liquid from a preselected sample container 28 at a specific position in the autosampler tray 21. When the needle 30 has drawn a sample in solution to be tested, it moves to the injection port 32 and injects the sample therein.

A supporting fluid container 34, adapted to contain a fluid such as a physiological saline solution, is mounted within the Faraday cage 14. A waste collection container 36 is also mounted within the Faraday cage 14. A plurality of ducts connect the various components of the assembly together for the purpose of transporting fluids among them. For example, a duct 38 connects the supporting fluid container 34 to the peristaltic pump 26; a duct 39 connects the supporting fluid container 34 to the syringe pump 24; a duct 40 connects the needle 30 to the syringe pump 24; a duct 42 connects the valve 22 to the waste collection container 36; a duct 44 connects the peristaltic pump 26 to the multiple connection valve 22; a duct 48 connects the injection port 32 to the microperfusion chamber valve 22; a duct 50 connects the rinsing station 23 to the waste collection container 36; and a duct 52 connects the peristaltic pump 26 to the waste container 36.

Mounted on a separate table is an inverted microscope 54 (Nomarski optics, Olympus model IX-70) having a stage 56. The microscope itself is attached to the movable part of the table. At least one electronic micromanipulator 58 (Eppendorf) is also mounted on the microscope stage 56, and supports a patch pipette electrode holder 60 having mounted there on a preamplifier (headstage) 61 and a conventional patch pipette 62 and which may optionally hold other electrodes for completing voltage and current clamp loops. A microperfusion chamber plate 64 is mounted on the microscope stage 56 and includes a microperfusion chamber 72. A supply duct 66 connects an outlet from the multiple connection valve 22 to an inlet of the microperfusion chamber plate 64, and a waste duct 68 connects the waste port of the microperfusion chamber plate 64 to a vacuum source for removal of waste. The distance from the valve 22 outlet to the microperfusion chamber 72 is 10 cm to minimize the dead-space. The electrode within the patch pipette 63 and the reference electrode are both connected to the preamplifier (headstage) 61. Electrical wire 76 connects the preamplifier (headstage) 61 to the voltage amplifier 78. Electrical wire 77 connects a reference electrode within the microperfusion chamber 72 with the preamplifier (headstage) 61. Any further voltage or current clamp electrode wires are connected to the amplifier designed to establish the desired current or voltage gradient by the preamplifier (headstage) 61. The voltage amplifier 78 is in turn electrically connected to a computer 80 used to measure the electrical impulses indicating the passage of ions through ion channel proteins of the membrane or cell being tested. The electronic micromanipulator 58 carrying the patch pipette holder 60 is mounted on the right side of the microscope stage 56.

To obtain well-defined applications to cells or membranes and to utilize only small volumes of test samples and supporting liquids, the valve 22 outlet should be as close as possible to the microperfusion chamber, or to the ti-tube when this component is utilized. Therefore the autosampler itself is placed within the Faraday cage, as shown in FIG. 1, close to the head-stage (preamplifier) 61 of the patch clamp amplifier 78 and the patch pipette 62, which is in contact with the membrane being tested. This raises two potentially serious problems:

1) Electrical noise. The introduction into a Faraday cage of any device which has to be powered by an alternating voltage will result in a source of 50 Hz or 60 Hz electromagnetic radiation. This may easily be picked up by the electrode in the patch pipette 62 (working as an antenna), thus disturbing the current signal. However, careful grounding of all metallic parts of the entire setup to a common high-quality ground will essentially solve this problem. Special care must be taken to ground and shield critical parts of the autosampler 20 to avoid excess electrical noise. When using other autosamplers, which possibly may be more difficult to ground effectively than the Gilson model utilized in the set-up shown in FIG. 1, it may become necessary to shield the autosampler in a separate Faraday cage.

2) Vibrations. Vibrations are created by the autosampler 20 when the needle 30 moves between sample containers 28. This has two implications: 1) Vibrations transferred to the pipette 62 will inevitably destroy the giga-seal (giga-ohm seal) in cell-attached as well as in whole cell recording modes. 2) Even weak mechanical vibrations may be transduced into low-frequency electrical noise appearing in the current signal. However, with the bridge set-up illustrated in FIG. 1, both problems are avoided.

The procedure is carried out by placing a membrane having ion channels into the microperfusion chamber 72. The patch clamp procedure may be more conveniently carried out by inserting a small coverslip 74 (2.8 millimetre), on which the cultured cells may be positioned within the microperfusion chamber 72. The patch electrode pipette 62 is then lowered into the microperfusion chamber 72 until it comes into contact with the membrane supported on the small coverslip 74. Suction is applied to the patch pipette 62 until a giga-seal (giga-ohms) is created between the end of the patch pipette 62 and the biological membrane. Testing is then carried out. An electrical signal is detected by an electrode in the patch pipette 62 attached to the preamplifier (headstage) 61, and then is transmitted by electrical wire 76 to the voltage amplifier 78 and the computer 80, shown in FIG. 1. A reference electrode (not shown) in contact with the solutions in the chamber is connected to the ground terminal of the preamplifier (headstage) 61.

Various supporting solutions can be adapted for use in the patch clamp procedure depending on the protocol appropriate for the compounds to be tested. A standard solution used for recording of calcium-activated potassium channels comprises (in mM) 140 KCl, 1 $CaCl_2$, 1 $MgCl_2$, 1.3 EGTA, 10 HEPES. This composition results in a free calcium concentration in solution of 0.3 $\mu$M. Calcium ion-induced K-channel activation can be achieved by changing the EGTA concentration to 1.07 mM, resulting in a free calcium concentration in solution of 1.0 $\mu$M. Test compounds are dissolved in the supporting solution depending on the protocol of he assay chosen. All test compound solutions and physiological saline solutions are filtered before use in the apparatus.

In the continuous flow adaptation of the technique and referring to FIG. 1, a continuous flow of the supporting liquid is established by the peristaltic pump 26. Periodically, the autosampler 20 aspirates a specified volume of test compound from a chosen sample vial 28 and loads it into a tubular loop 70 (total loop filling) via injection port 32. The sample volume, loop volume, flow rate, etc. are optional. After loading, the outlet of the multiple connector valve 22 changes and the loop content is conducted by the duct 66 from the valve to the microperfusion plate into the microperfusion chamber 72 from which excess fluid is removed by aspiration. The duration of test compound application is determined by the loop size and the flow rate. The wash out time of the compound is optionally determined by the period between injections. The autosampler changes chamber solutions automatically according to a predefined program. The number of compounds tested between washout periods varies according to the chosen protocol.

The specific advantages of the present continuous flow system compared to more conventional continuous flow Systems, are:

1) Automatic change of test-solutes.
2) Extensive and flexible coordination between autosampler and patch clamp amplifier.
3) Flexibility of compound application, change of programs during experiments, etc.
4) Automatic dissolution of compounds just prior to the testing of the compound (important for unstable materials).
5) Automatic rinsing of needle and injection port to avoid carry over between individual applications.

Figure 2:
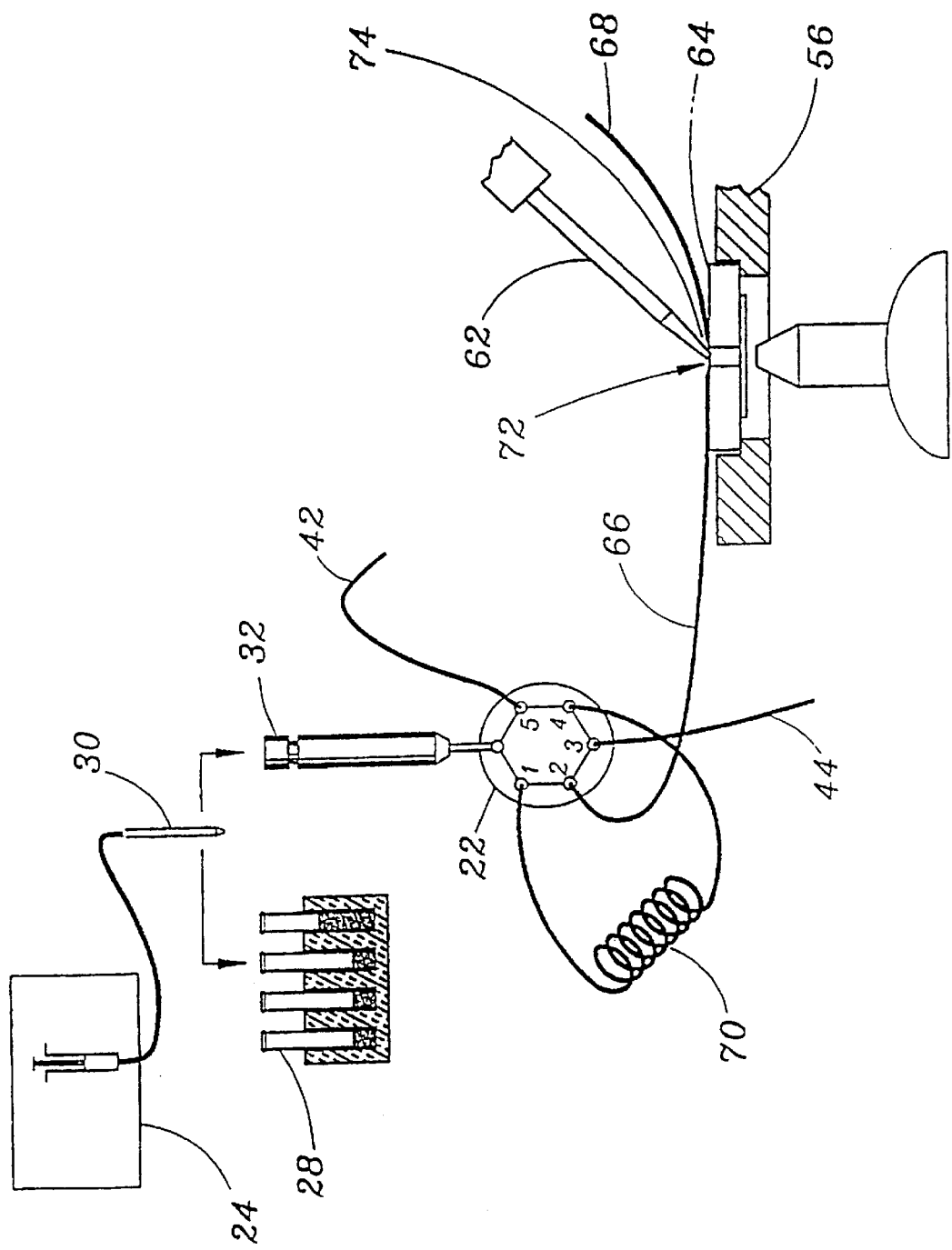
FIG. 2 is a schematic view of a portion of the apparatus as it is utilized in practising the continuous flow technique of the present invention.

Referring to FIG. 2, the details of the continuous flow technique utilizing the apparatus shown in FIG. 1 are shown in schematic diagram. In operation, a physiological saline solution, or other supporting liquid is pumped at a steady rate by the peristaltic pump 26 through the valve 22 and on to the microperfusion chamber 72. Fluid is also continuously aspirated by vacuum from the microperfusion chamber 72 via the duct 68. The procedure continues as follows:

a) A small volume of air is aspirated into the needle 30 by the syringe pump 24.
b) The needle 30 is moved to a sample vial 28 and aspirates a specified volume of sample.
c) The needle 30 is moved to the injection port 32 and loads the tubular loop 70 with the sample (usually 3 times loop volume; excess volume is rejected through outlet 5 of the multiple connector valve 22).
d) The multiple connector valve 22 changes to the injection mode and the tubular loop 70 content is injected into the duct 66 from the valve 22 to the microperfusion chamber 72.
e) The multiple connector valve 22 changes to the continuous flow mode and the saline solution continues to flow after the sample aliquot being tested.
f) Before the next application is initiated, the needle 30 is rinsed (perfusion on both sides with reservoir solution) in the rinsing station 23. Reservoir solution is drawn up from the supporting fluid container 34 through the duct from the supporting fluid container 39 and discarded through the needle 30 at the rinsing station 23. The injection port 32 is rinsed by loading reservoir saline through the valve 22 with waste solution discarded through outlet 5.

Figure 3:
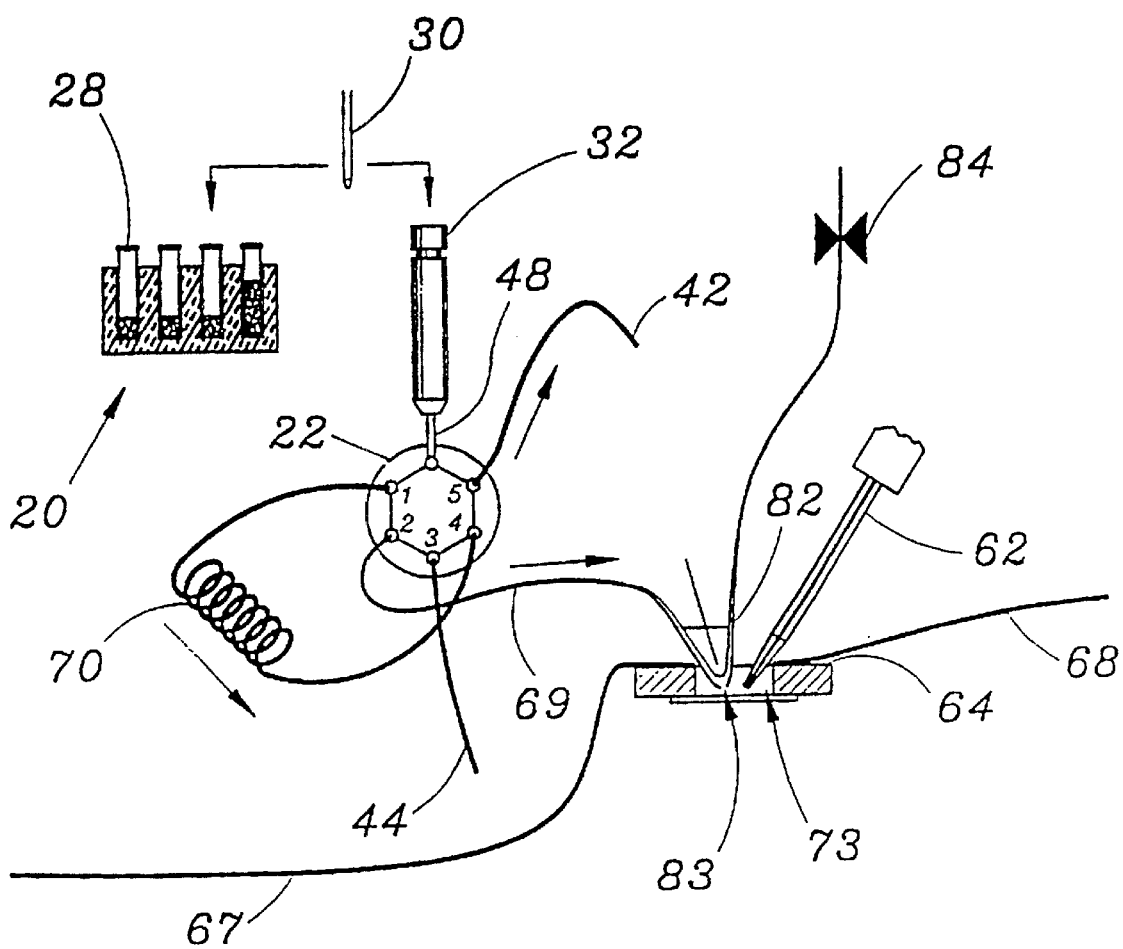
FIG. 3 is a schematic view of a portion of the apparatus as it is modified and utilized in practising the UTube technique of the present invention.

Referring to FIG. 3, a modified embodiment of the invention is shown which is utilized to carry out the U-tube technique. The component utilized in carrying out the method of this embodiment are substantially the same as those shown in FIG. 1, with the exception that the test sample is discharged into the perfusion chamber 73, through an aperture 83 provided in the bottom of a U-tube 82.

Conventional fast application systems like the U-tube system are easily served by the apparatus of the present invention, including the autosampler. Cells are placed in a somewhat larger perfusion chamber than that used in the continuous flow technique described above. This facilitates positioning of the U-tube. The autosampler operates in the U-tube technique in much the same manner as it operates in the continuous flow technique described above. The membrane is continuously perfused by normal saline solution pumped at a steady rate by the peristaltic pump 26 through a duct 67 from the peristaltic pump 26 to the perfusion chamber 73 (this duct does not pass through the multiple connection valve 22). Fluid is also continuously aspirated from the perfusion chamber 73 via duct 68 and the peristaltic pump. The peristaltic pump also continuously pumps normal saline through the U-tube 82. The fluid is pumped through the multiple connection valve 22 and on to the U-tube through duct 69. Because of the reduced pressure within the U-tube resulting from the fluid flow, a small amount of fluid from the perfusion chamber 73 is aspirated through the aperture 83 into the U-tube. As in the continuous flow method, a drug sample is loaded into the tubular loop 70. The multiple connector valve 22 changes to the injection mode and the tubular loop 70 content is injected into the duct 69 from the outlet port of the multiple connector valve 22 to the U-tube 82. The magnetic valve 84 at the outlet of the U-tube 82 is closed, which causes an increase in pressure within the U-tube, thereby forcing a portion of the drug sample through the aperture 83 and into the perfusion chamber 73. After the test of the drug sample is completed, the valve 84 is reopened, stopping the further flow of the drug sample through the aperture 83. The continuous aspiration of the perfusion chamber quickly flushes away the drug sample from the perfusion chamber.

The application time is option and determined by the period the valve is closed. The use of the U-tube requires a larger experimental perfusion chamber, as shown in FIG. 3. The U-tube is placed on 8 separate micromanipulator and positioned under visual guidance from the microscope.

The advantage of the U-tube system is that it combines the fast application time needed for studying transmitter regulated channels with the high capacity and low volume requirement of the autosampler.

FIG. 3 shows the flow pattern as it takes place with the U-tube system. This pattern is essentially the same as that in the continuous flow technique, described above. In operation, saline solution is pumped at a steady rate by the peristaltic pump 26 through a duct 67 from the peristaltic pump 26 to the perfusion chamber 73 (this duct does not pass through the multiple connection valve 22). Fluid is also continuously aspirated from the perfusion chamber 73 via duct 68 and the peristaltic pump. The peristaltic pump also continuously pumps normal saline through the U-tube 82. The fluid is pumped through the multiple connection valve 22 and on to the U-tube through duct 69. The general procedure is as follows:

a) A small volume of air is aspirated into the needle 30 by the syringe pump 24, shown in FIG. 1.
b) The needle 30 is moved to a sample vial 28 and aspirates a specified volume of sample.
c) The needle 30 is moved to the injection port 32 and loads the tubular loop 70 with the sample (usually 3 times loop volume; excess volume is rejected through outlet 5).
d) The multiple connector valve 22 changes to the injection mode and the tubular loop 70 content is injected into the duct 69 from the outlet port of multiple connector valve 22 to the U-tube 82.
e) Application occurs by closure of the U-tube outlet by the magnetic valve 4.
f) Upon reopening of magnetic valve 84, the flow of normal saline displaces the sample in the U-tube. The sample solution is flushed from the perfusion chamber 73 by the continuous flow of normal saline pumped from duct 67 and aspirated through duct 68.
g) Before the next application is initiated, the needle 30 is rinsed (perfusion on both sides with reservoir solution) in the rinsing station. The injection port 32 is rinsed by loading reservoir saline through the valve 22 with waste solution discarded through outlet 5.

In order to limit the solution volume and the test compound requirement to an absolute minimum, a stop flow technique according to the present invention was developed.

Figure 4:
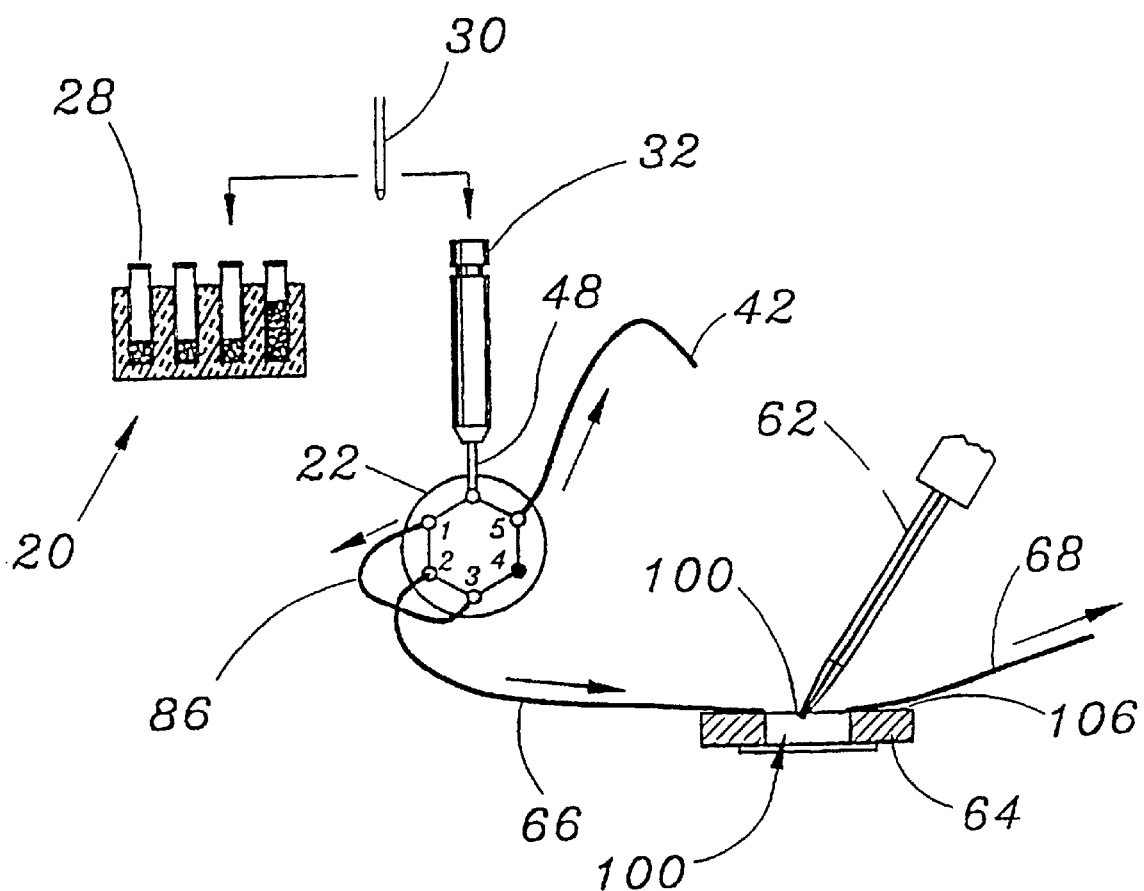
FIG. 4 is a schematic view of a portion of the apparatus as it is modified and utilized in practising the stop flow technique of the present invention.

Referring to FIG. 4, a somewhat modified arrangement of some of the components is shown for practising the stop flow technique. The total volume of the dead space including the injection port 32, the multiple connector valve 22, and the tubing is now particularly critical. Consequently, the tubular loop 70 is replaced with a short straight piece of tubing 86 in order to shorten the path of the test solution and thereby reduce the volume of solution required. The volume is reduced to 15 $\mu$l by a special connection of valve inlets and outlets (no loop). In this adaptation the operation of the autosampler is somewhat different from that utilized in HPLC autosamplers. However, the general principle is simple, namely, that the autosampler aspirates a specified volume from a sample vial and loads it directly into the microperfusion chamber 100. The process takes place as follows:

a) A small volume of air is aspirated into the needle 30 by the syringe pump 24, shown in FIG. 1.
b) The peristaltic pump 26, shown in FIG. 1, is automatically activated just before injection, and excess fluid in the microperfusion chamber 100 is aspirated.
c) The needle 30 is moved to a sample vial 28 and aspirates 200 $\mu$l of test solution (control solution+test compound) or saline solution alone.
d) The needle 30 is moved to the injection port. Using the "partial loop filling" option of the sampler, the first 20 $\mu$l injected (which possibly contain air-bubbles) is discharged through a waste valve outlet 5 and duct 42.
e) The valve is turned and the remaining solution, 180 $\mu$l, is loaded directly to the microperfusion chamber 100 (loading time 15 sec., but in principle optional) with continuous aspiration of excess volume from the chamber 100 by duct 68.
f) After injection, the pump and the liquid flow are stopped for the required period and the necessary electrical measurements are made as an indication of the amount of ion transfer, and the value recorded by the computer.
g) Before the next application is initiated, the needle 30 is rinsed (perfusion on both sides with reservoir solution) in the rinsing station, the injection port 32 is rinsed by loading reservoir saline solution through the outlet 5 of the valve 22.

The advantage of the stop flow system is primarily a very low sample volume requirement (maximally 220 $\mu$l total). If less perfusion than around 20 times chamber volume is acceptable, the total volume may be decreased accordingly. Experiments performed according to the present invention indicate that more than 90% exchange is obtained by injecting just 100 μl (140 μl total). Such a low volume requirement permits the electrophysiological testing of entire chemical libraries, often based on small amounts of compounds from synthesis and/or isolates from natural products.

Additionally, according to the present invention, several embodiments of microperfusion chamber assemblies have been developed having extremely small microperfusion chambers. The use of these microperfusion chambers provides a system for analysing extremely small volumes of test samples and supporting liquids, thereby greatly reducing the time required for the testing procedure.

Figure 5:
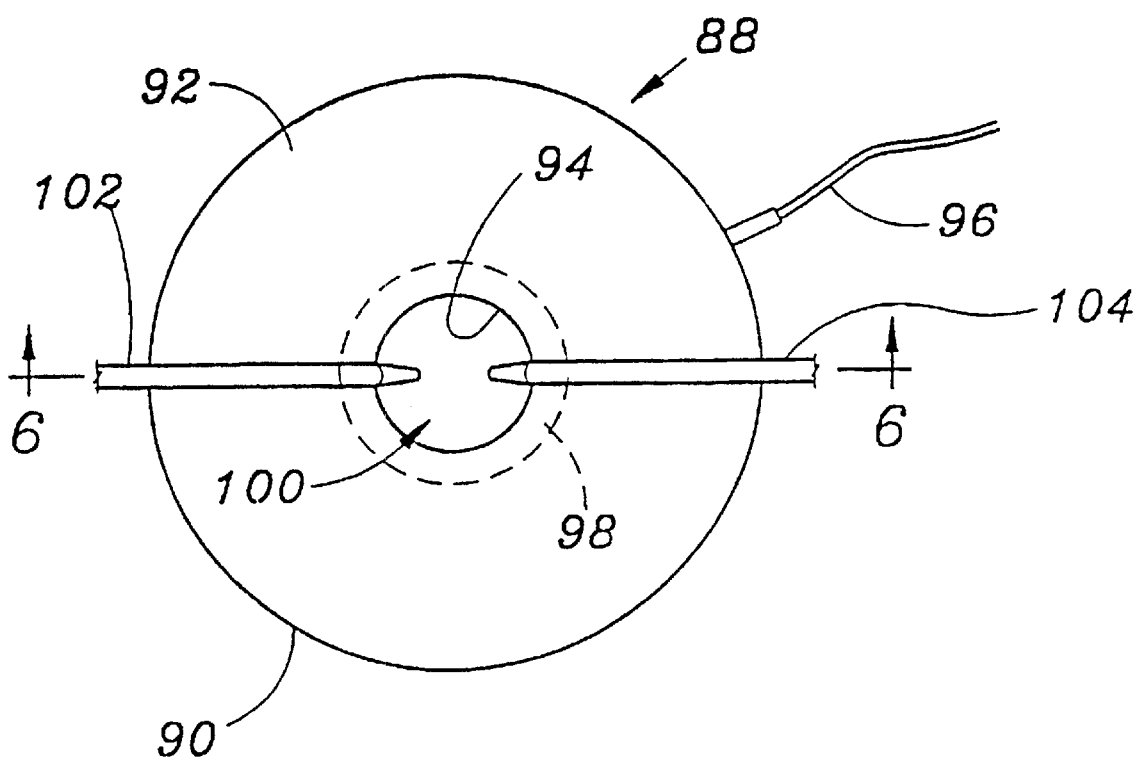
FIG. 5 is a plan view of a microperfusion chamber plate according to one form of the invention.
Figure 6:
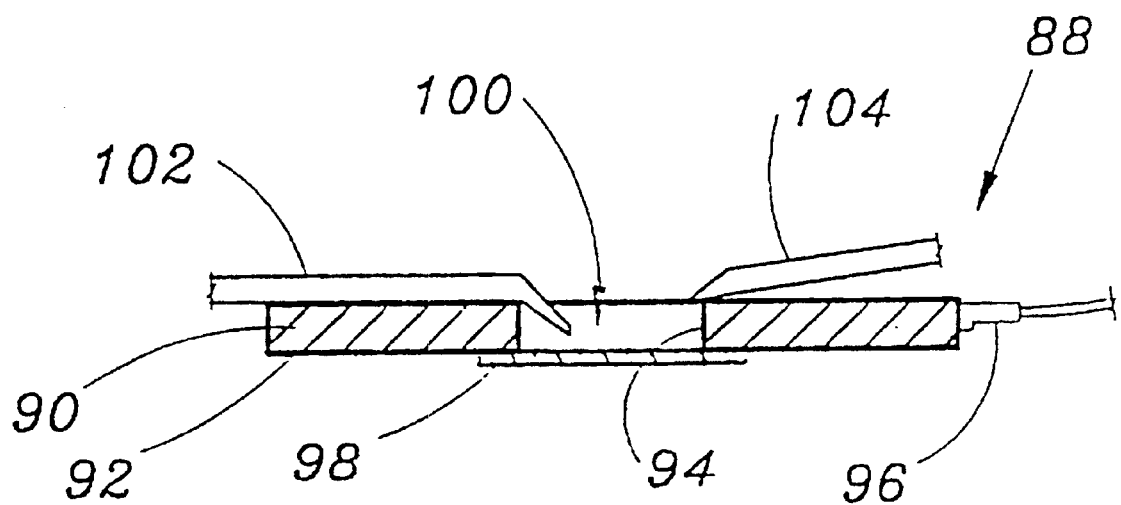
FIG. 6 is a cross-sectional view of the microperfusion chamber plate shown in FIG. 5, taken at the line 6—6 of FIG. 5.

Referring to FIGS. 5 and 6, one embodiment of a very small volume microperfusion chamber assembly 88 is shown. Because of the extremely small size of the chamber, there is insufficient space for two electrodes to be Positioned in the microperfusion chamber 100. Consequently, the reference electrode must be an integral part of the chamber structure. In the embodiment shown in FIGS. 5 and 6, the chamber assembly 88 comprises a silver disk 90 coated with a thin layer of silver chloride 92. The silver disk 90 and the silver chloride layer 92 cooperate to serve as a reference electrode. The silver disk 90 has a thickness of 1 mm, and a diameter of 6 mm. A 3 mm aperture 94 is bored into the centre of the disk to form the microperfusion chamber 100 cavity. A silver wire 96 is soldered to the silver disk 90. The silver chloride layer 92 is applied to the surface of the silver disk 90 by placing the silver disk 90 in an aqueous solution of sodium chloride and electrolyzing the disk for 2 hours while it is connected as the anode and utilizing a separate silver wire as the cathode. In order to prevent shorting out of the electrode at least the entire surface of the aperture 94 should be coated with silver chloride. Preferably, the entire silver disk 90 is coated with silver chloride, including the surface of the aperture 94. A glass coverslip 98, 40 mm in diameter and 0.1 mm thick, is adhesively affixed to the bottom of the coated silver disk 90 and over the aperture 94, to form a transparent bottom of the microperfusion chamber 100. The volume of the microperfusion chamber 100 may be in the range of 5–50 μl. More desirable results may be obtained with a microperfusion chamber 100 in the range of 10–15 μl, although the preferred range is 10–12 μl in order to utilize only small samples of the material to be tested and small volumes of supporting liquid, thereby reducing the time required for each test. All solutions enter the chamber through inlet 102 and are aspirated from the chamber through outlet 104.

Cultured cells may be grown in monolayers on small coverslips 74 (thickness 0.1 mm, diameter 2.6 mm) in a standard incubator. Prior to carrying out the experiments, a single coverslip 74 is transferred by thin forceps to the bottom of the microperfusion chamber 100 and superfused with saline. The patch pipette 62, shown in FIG. 1, a standard patch clamp having a final resistance of 2–6 MΩ, is lowered from above -as indicated in FIGS. 1, 2, 3, and 4. The patch pipette 62 has a silver-silver chloride electrode 63 mounted therein, and is supported by the patch pipette holder 60, a standard type developed by HEKA Electronics. The diameter of the pipette tip is about 1 μm. Consequently, when the pipette is filled by suction, and back-filling, the solution stays in place due to capillary force. Only a slight suction applied by mouth is necessary for creating a gigaseal between the pipette and the membrane used in the testing. The electrode 63 contained in the patch pipette 62 is electrically connected to the preamplifier (headstage) 61, which is in turn electrically connected to the patch clamp amplifier 78, which is in turn electrically connected to the computer 80. The silver wire 96 is electrically connected to the reference electrode, which comprises the silver disk 90 and the silver chloride layer 92. The reference electrode is connected to the silver wire 96, which is in turn electrically connected to the ground terminal on the preamplifier (headstage) 61.

The effect of each sample being tested on ion channel transfer is measured in terms of electrical current flow by the electrode contained in the patch pipette 62 and the reference electrode, and recorded by the computer 80.

Figure 7:
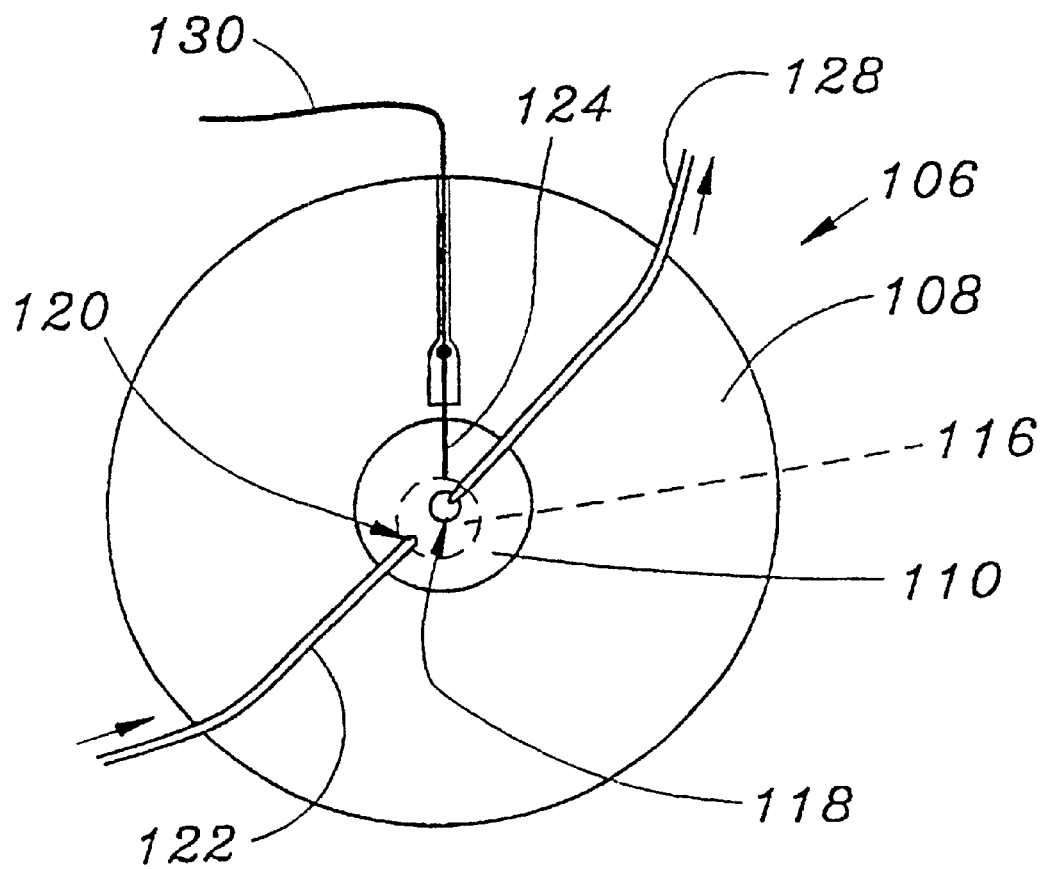
FIG. 7 is a plan view of a microperfusion chamber plate assembly according to another embodiment of the invention.
Figure 8:
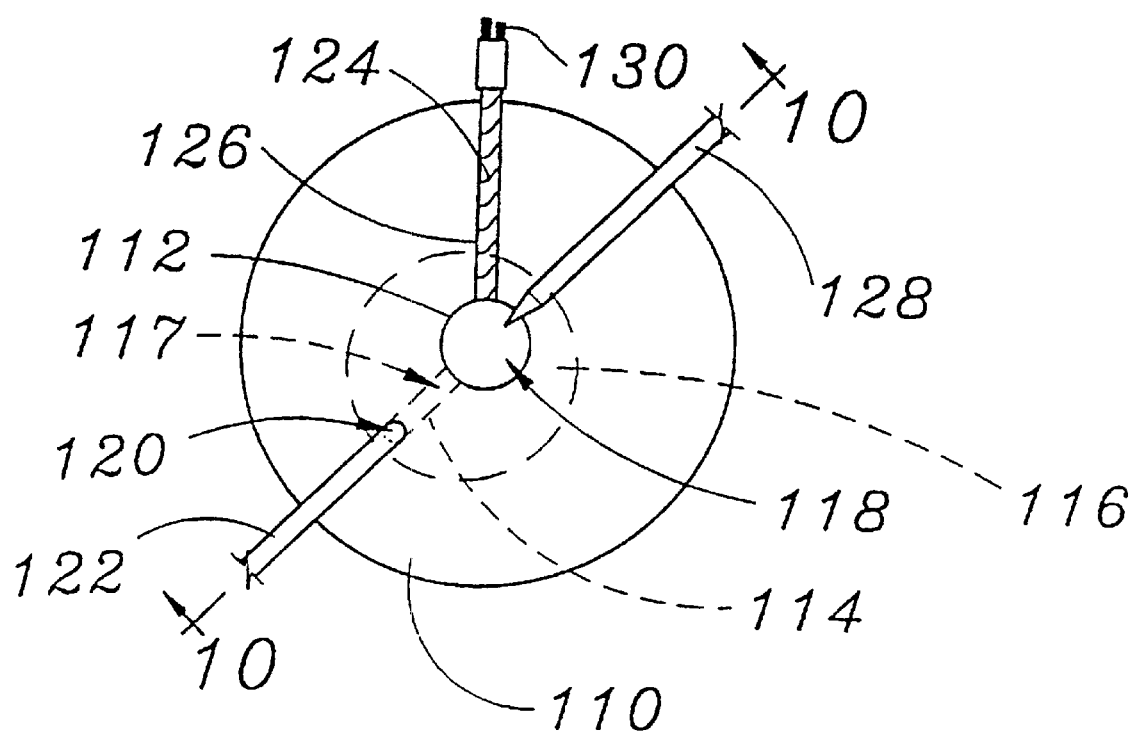
FIG. 8 is a top plan view of the microperfusion chamber plate of the assembly shown in FIG. 7.
Figure 9:
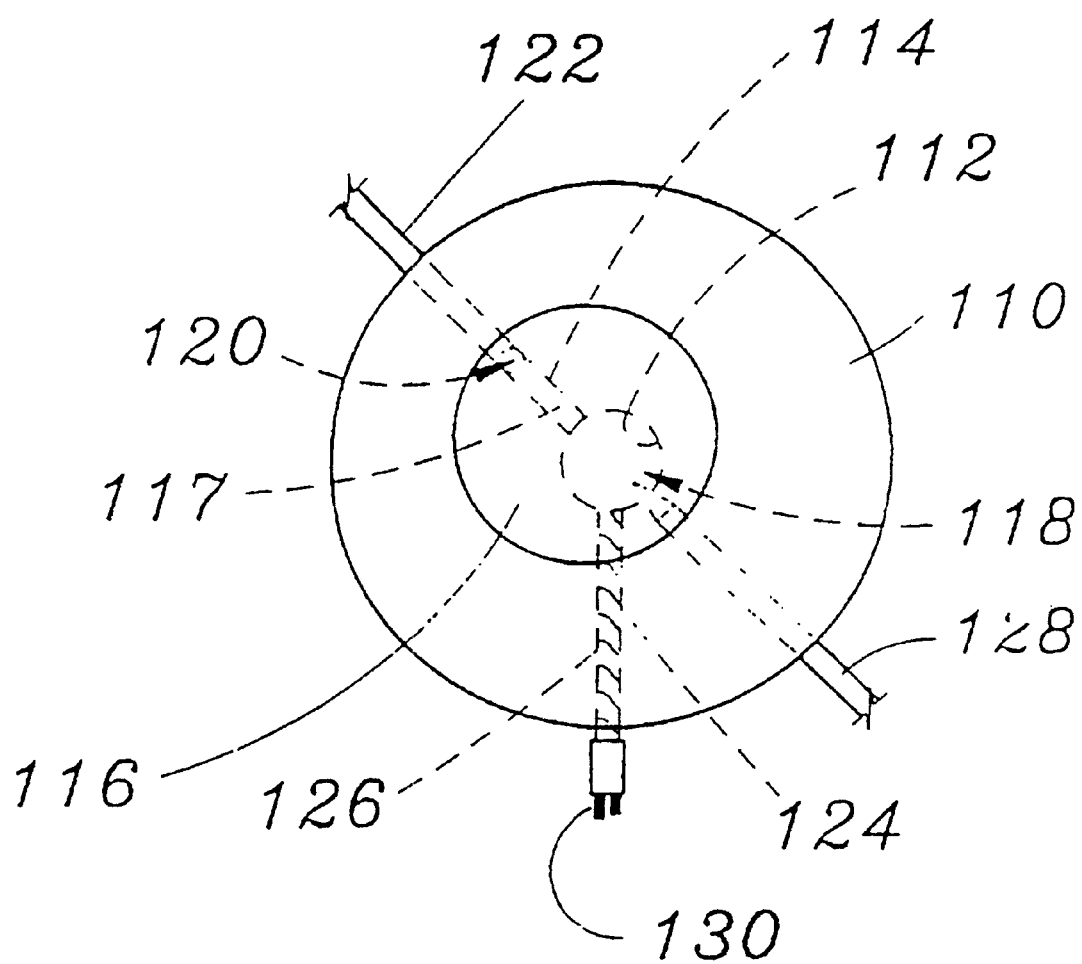
FIG. 9 is a bottom plan view of the microperfusion chamber plate of the assembly shown in FIG. 7.
Figure 10:
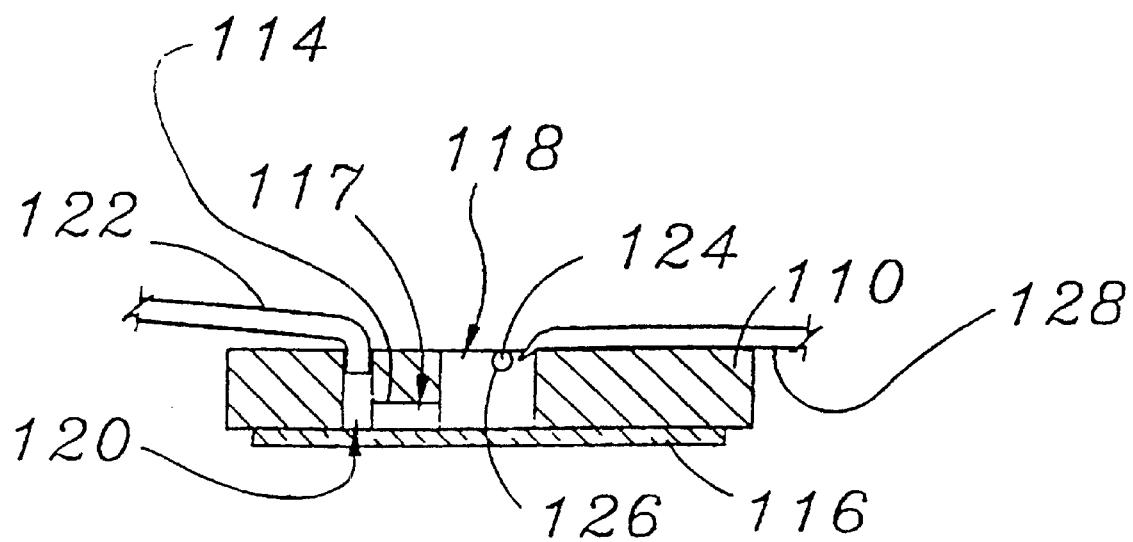
FIG. 10 is a cross-sectional view taken at the line 10—10 of FIG. 8.

Referring to FIGS. 7, 8, 9, and 10, a microperfusion chamber assembly 106 in another embodiment is shown. As shown in FIG. 7, the assembly 106 comprises a metal sup-25 porting disk 108 designed to fit exactly into the central aperture of the microscope stage 56. Mounted in an aperture provided in the supporting disk 108 is a microperfusion chamber disk 110, shown in detail in FIGS. 8 and 9. The microperfusion chamber disk 110 may be made of any non-electrically conducting materials, among which are plastics including methyl methacrylate, polystyrene, polyvinyl chloride, phenol formaldehyde, or many other materials. An aperture 112 is drilled into the microperfusion chamber disk 110 having a diameter of about 3 mm. A groove 114 is provided in the bottom of the microperfusion chamber disk 110 and a coverslip 116 is cemented to the bottom of the disk 110. The coverslip 116 cooperates with aperture 112 to form a microperfusion chamber 118. The coverslip 116 cooperates with the groove 114 to form a channel 117 for introducing the liquid sample to be tested and the supporting saline solution into the microperfusion chamber 118. An aperture 120 is provided in the upper wall of the disk 110 to serve as a port for the introduction of liquids into the channel 117. A tube 122 connects the aperture with the autosampler multiple connection valve 22 shown in FIG. 1. A small silver/silver chloride pellet electrode 124 is embedded in a groove 126 provided in the upper surface of the disk 110, and serves as a reference electrode. The pellet electrode 124 is formed of a mixture of silver and silver chloride compressed around a silver wire, obtained from IN VIVO METRIC, California. A wire from the electrode 124 is connected directly to the amplifier headstage 78, shown in FIG. 1.

Aspiration of excess fluid from the microperfusion chamber such as 72, 100, or 118 represents a special problem with small chambers, since a large fraction of the total chamber volume is aspirated per second. A very smooth aspiration with a tiny plastic tube 128 (Eppendorf GELoader Tip) can be utilized and is essential to avoid fluctuations in the level of the liquid surface. Unstable liquid surfaces produce a variable background noise and may also confer an increased mechanical stress to the cell or patch, thereby limiting the recording period.

The following examples, given by way of illustration only and not by way of limitation, will provide a clear understanding of the manner in which the invention can be performed.

EXAMPLE 1

CONTINUOUS FLOW TECHNIQUE: The calcium current, of a chick dorsal root ganglion cell was determined in whole-cell recording using the continuous-flow technique utilizing an apparatus as disclosed above and diagrammed in FIGS. 7–10, comprising an autosampler, syringe pump, peristaltic pump, and microperfusion chamber having a volume of 12 μl.

The $Ca^{2+}$ currents were isolated from other currents by use of the following pipette and bath solutions:

Pipette: CsCl (100 mM), CsF (20 UIM), EGTA (10 mM), $MgCl_2$ (4 mM), HEPES (10 mM).

Bath: NaCl (140 mM), KCl (4 mM), $CaCl_2$ (2 mM), $MgCl_2$ (1 mM), HEPES (10 mM), TTX (0.3 pM). The high Calcium concentration blocks K+ currents, whereas TTX (tetrodotoxin) blocks Na+ currents.

Figure 11:
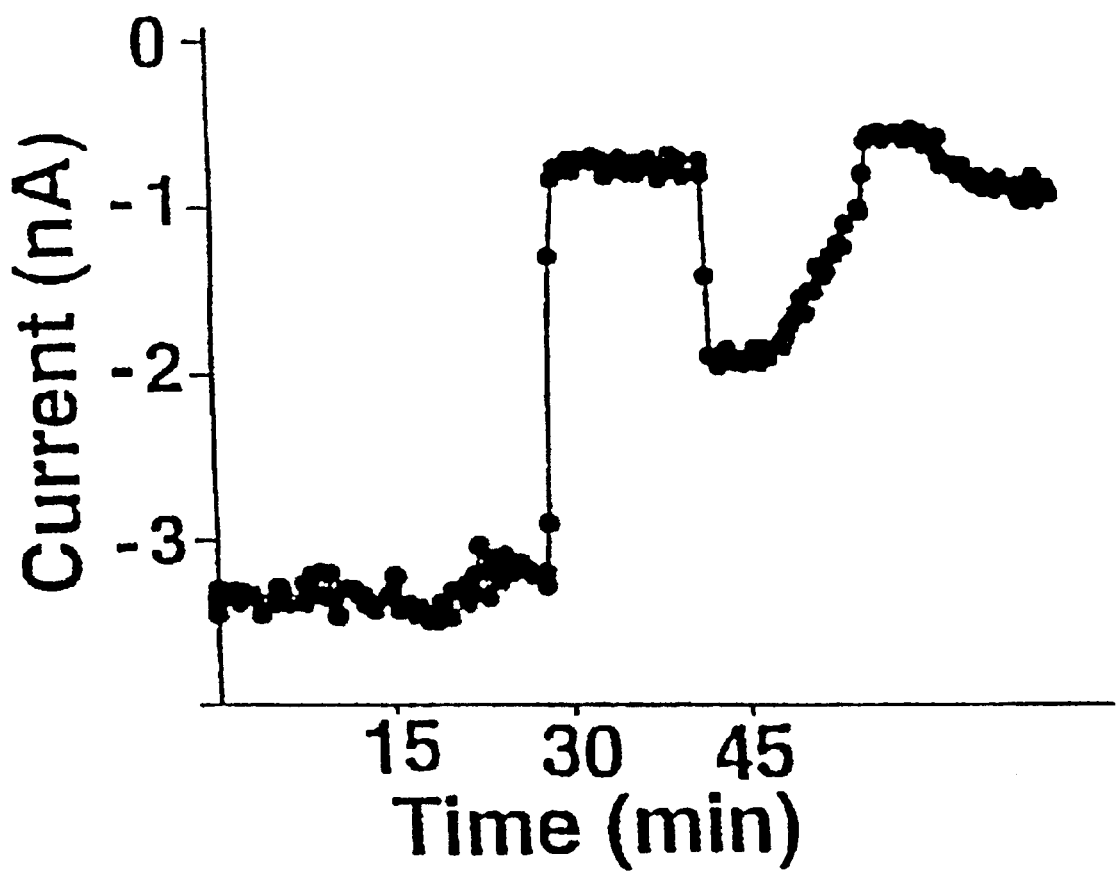
FIG. 11 is a graph displaying the effect of reference compounds on voltage dependent calcium channels.

The effects of five known standards, phenytoin, amiloride, w-conotoxin MVIIA, Bay-k 8644, and nifedipine on voltage dependent calcium channels were tested in sequence and are reported in FIG. 11. The graphical presentation indicates successive recordings of the maximum current induced by 5 msec depolarizing voltage steps to 0 mV from the −70 mV resting potential. The compounds were perfused in 500 µl aliquots. Neither phenytoin nor amiloride, injected at the 0 and 15 minute timepoints respectively, affected the current, indicating no effect on calcium ion channels. At the 30 minute timepoint, a 500 µl aliquot of w-conotoxin MVIIA was injected. The (1)-conotoxin MVIIA has a high affinity for N-type calcium channels as demonstrated by the current modulation recorded on the graph. The graph also demonstrates that the (i}-conotoxin MVIIA binding was irreversible because no washout is evident from the graph. Bay-k 8644 and nifedipine were injected at 45 minutes and 1 hour respectively. Bay-k 8644 stimulates L-type calcium channels reversibly, as is evident from the washout over time. Nifedipine blocks the L-type calcium channel.

The invention is thus demonstrated to be useful in determining the response of patch-clamp isolated membrane ion channels to perfusion with compounds having well-know physiological activity. The results indicate that five compounds were tested in little more than one hour using a single membrane preparation, and exhibiting a useful range of physiological response. In practice, screening of unknown compounds including application periods as well as washout periods between applications are shorter and therefore ten to twenty compounds can be screened in the course of an hour. (See especially Example 2.)

EXAMPLE 2

STOP-FLOW TECHNIQUE: The potassium current of a cultured human coronary smooth muscle cell was determined in an excised inside out patch by the stop- flow technique utilizing an apparatus as disclosed above and diagrammed in FIGS. 7–10, comprising an autosampler, syringe pump, and microperfusion chamber having a volume of 12 µl.

The composition of the pipette and bath solutions was:

Pipette: KCl (140 mM), $CaCl_2$ (1 mM), $MgCl_2$ (1 mM), EGTA (1.3 mM), HEPES (10 mM).

Bath: KCl (140 ZuM), $CaCl_2$ (1 mM), $MgCl_2$ (1 mM), EGTA from 1.07 mM to 2.0 mM. The free $Ca^{2+}$ concentration is determined by the concentration of EGTA. All test compounds were dissolved in bath solution with 0.3 pM free Ca2+.

Figure 12:
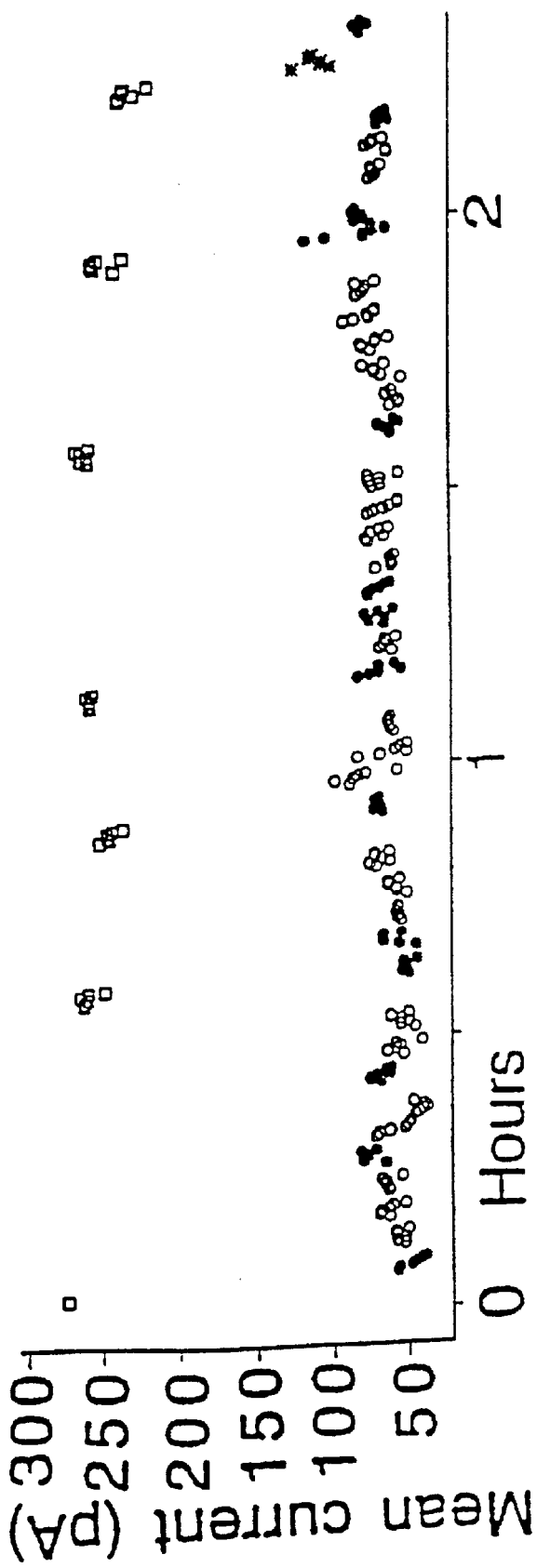
FIG. 12 is a graph displaying the effect of test compounds on calcium-activated potassium channels.
Figure 13:
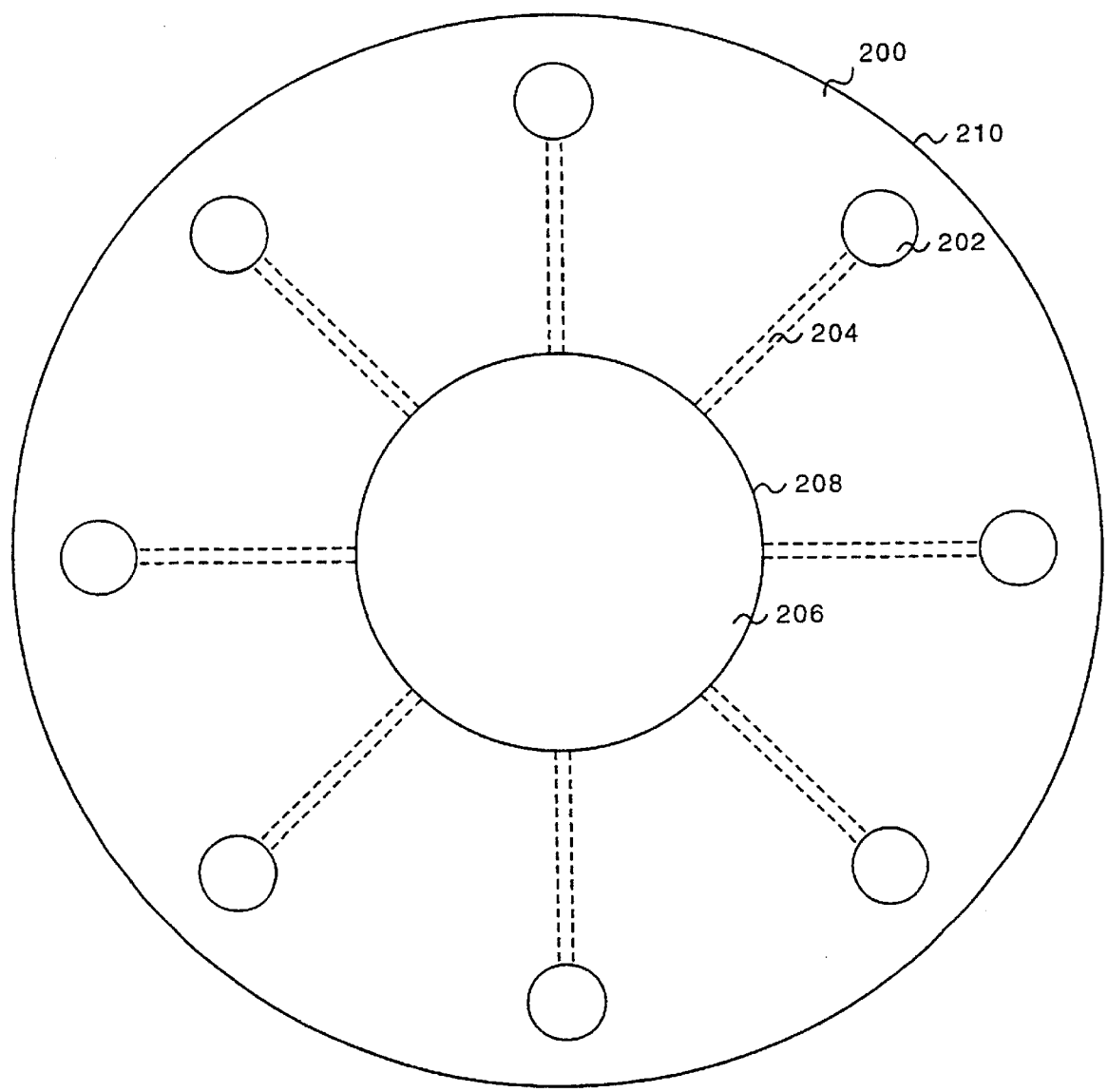
FIG. 13 is a schematic view of a rotatable outer part of a turn table comprising several perfusion chambers.
Figure 14:
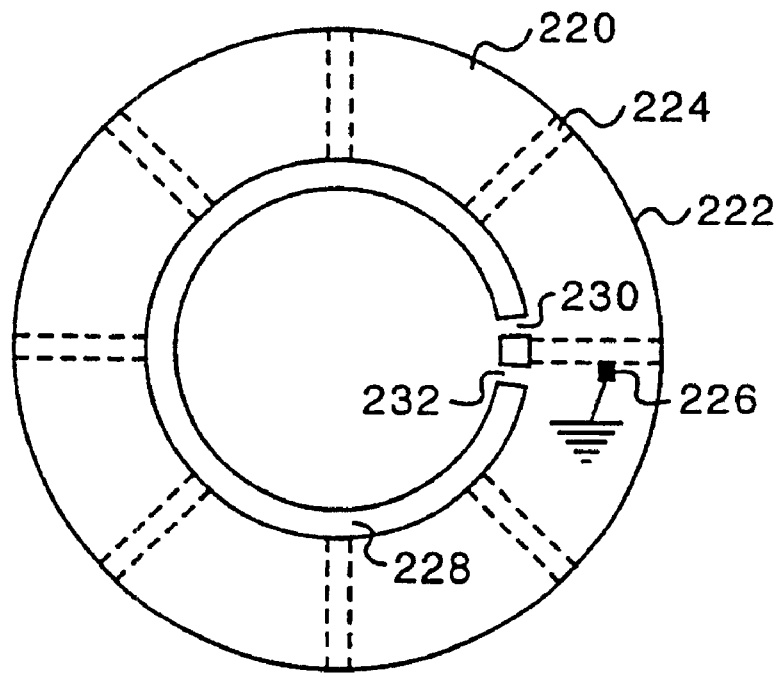
FIG. 14 is a schematic view of a fixed inner part of a turntable comprising several perfusion chambers.
Figure 15:
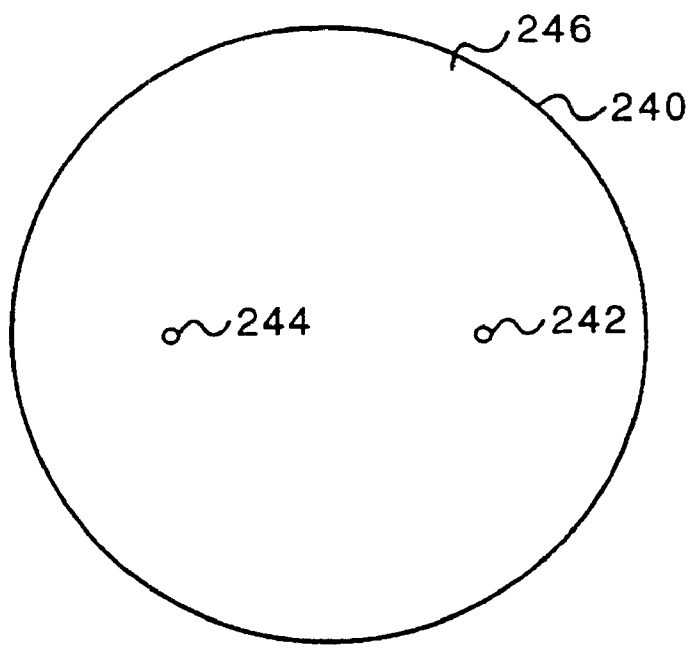
FIG. 15 is a schematic view of a top part of a turntable comprising several perfusion chambers.

The effects of 25 unknown compounds on calcium activated potassium channels were tested and reported in FIG. 12. In the experimental protocol, successive unknown compounds (open circles) were perfused (300 µl) with intermittent washout with saline solution (filled circles). Each application lasted 2 minutes and is reported as six (6) data points. Multiple channels were present in the patch and their activity was adjusted to a low level (20% of full activity) by a bath solution having a low free calcium ion concentration (0.3 µM). This level was chosen to be able to detect both possible activating and blocking effects of the unknown test compounds. At various intervals full activation was induced by perfusion with saline solution containing 1 µM free calcium ion concentration (open squares). Perfusion with saline solution containing 0.5 µM free calcium ion was tested at the end (asterisk *). In this particular test of 25 unknowns at a concentration of 1 µM, no compound induced a change from the basal calcium activated potassium current, but the potassium channels of the membrane preparation exhibited characteristic high potassium current when exposed to the high (1.0 µM) calcium concentration saline solution.

The invention is thus demonstrated to provide a mechanism whereby small volumes of test compounds can be analyzed in rapid succession. The test is remarkable because over twenty-five (25) unknown test compounds were screened in the course of a two hour time period. The test was validated by intermittent full activation of K-channels induced by perfusion with saline solution having a higher free calcium ion concentration. This high calcium induced potassium current demonstrates the scope of current response available from the membrane preparation, evidencing the sensitivity necessary to detect an active compound.

The present invention provides a novel way of utilizing an HPLC autosampler in carrying out patch clamp techniques. This enables a large number of tests to be carried out in a relatively short time period. The invention also comprises the use of novel microperfusion chamber assemblies containing very small microperfusion chambers, thereby enabling very small amounts of test sample solutions and supporting solutions to be utilized, and additionally reducing the amount of time required for each test. The invention also includes several novel procedures for carrying out the patch clamp technique providing even further benefits. The invention further includes novel microperfusion chamber structures utilizing very small chambers and having integral electrodes.

In the following claims, the term "membrane" is employed to designate whole cells or partial cell membranes.

Although preferred embodiments of the invention have been illustrated in the accompanying drawings and described in the foregoing Specification, it is to be understood that the invention is not limited to the exact embodiments disclosed or to the exact details of operation or exact methods or procedures shown and described, since the invention is capable of numerous modifications, rearrangements, and substitutions of parts and elements and other equivalents, without departing from the spirit or scope of the invention, as will readily be apparent to one skilled in the art, wherefore the present invention is to be understood as limited only by the full scope which can be legally accorded the appended claims.

Referring to FIGS. 13—18, a turn table 400 comprising several perfusion chambers 202 is shown. The turn table 400 comprises three parts, a rotatable outer part 200, a fixed inner part 220 and a top part 246. The rotatable outer part 200 has an outer periphery 210, an inner periphery 208 defining an inner volume 206 within the periphery 208, and a plurality of perfusion chambers 202. Each of the perfusion chambers 202 is connected to the inner volume 206 through drilled bores 204 in the outer part 200. The plurality of perfusion chambers 202 with connecting drilled bores 204 is in a preferred embodiment eight, but fewer, such as four, as well as more, such as sixteen, perfusion chambers 202 may be provided.

The outer periphery 222 of the inner part 220 is slightly smaller than the inner periphery 208 of the outer part 200, i.e. the inner part 220 fits into the volume 206 of the outer part 200. The inner part 220 comprises a milled out grove 228 that communicates with the outer periphery 222 through a plurality of bores. The grove 228 has two stop points 230 and 232, as well as a reference electrode 226 connected to the internal of the grove 228 leading to a test perfusion chamber 202'. At the other end, the reference electrode 226 is grounded.

The top part 246 is a plate with an outer periphery 240 and two holes 242 and 244. In one embodiment of the invention, the periphery 240 of the top plate 246 has the same size as the outer periphery 222 of the inner part 220, but the periphery 240 of the top plate 246 could be made larger or smaller than the outer periphery 222 of the inner part 220, as long as the two holes 242 and 244 are positioned so as to provide connection from the upper side of the top part 246 through the top part 246 to the grove 228 in the inner part 220 when the top part 246 is mounted on the inner part 220.

Furthermore, when the inner part 220 and the top part 246 is mounted in the outer part 200 so that the drilled bores 224 in the inner part 220 is positioned in connecting relationship with the drilled bores 204 in the outer part 200, the hole 244 in the top part 246 is positioned so as to provide connection from the upper side of the top part 246 through the top part 246 into the grove 228 between the two stop points 230 and 232 and further out to the test perfusion chamber 202' in the other end of the connecting drilled bores 224 and 204. In this position, the hole 242 provides connection from the upper side of the top part 246 through the top part 246 into the grove 228 and from there to the rest of the perfusion chambers 202 via the drilled bores 204 and 224. In this turn table 400, one solution may be supplied to the test perfusion chamber 202' through the hole 224 and simultaneously another solution may be supplied to the other perfusion chambers 202 through the hole 242 without the two solutions being mixed.

Figure 16:
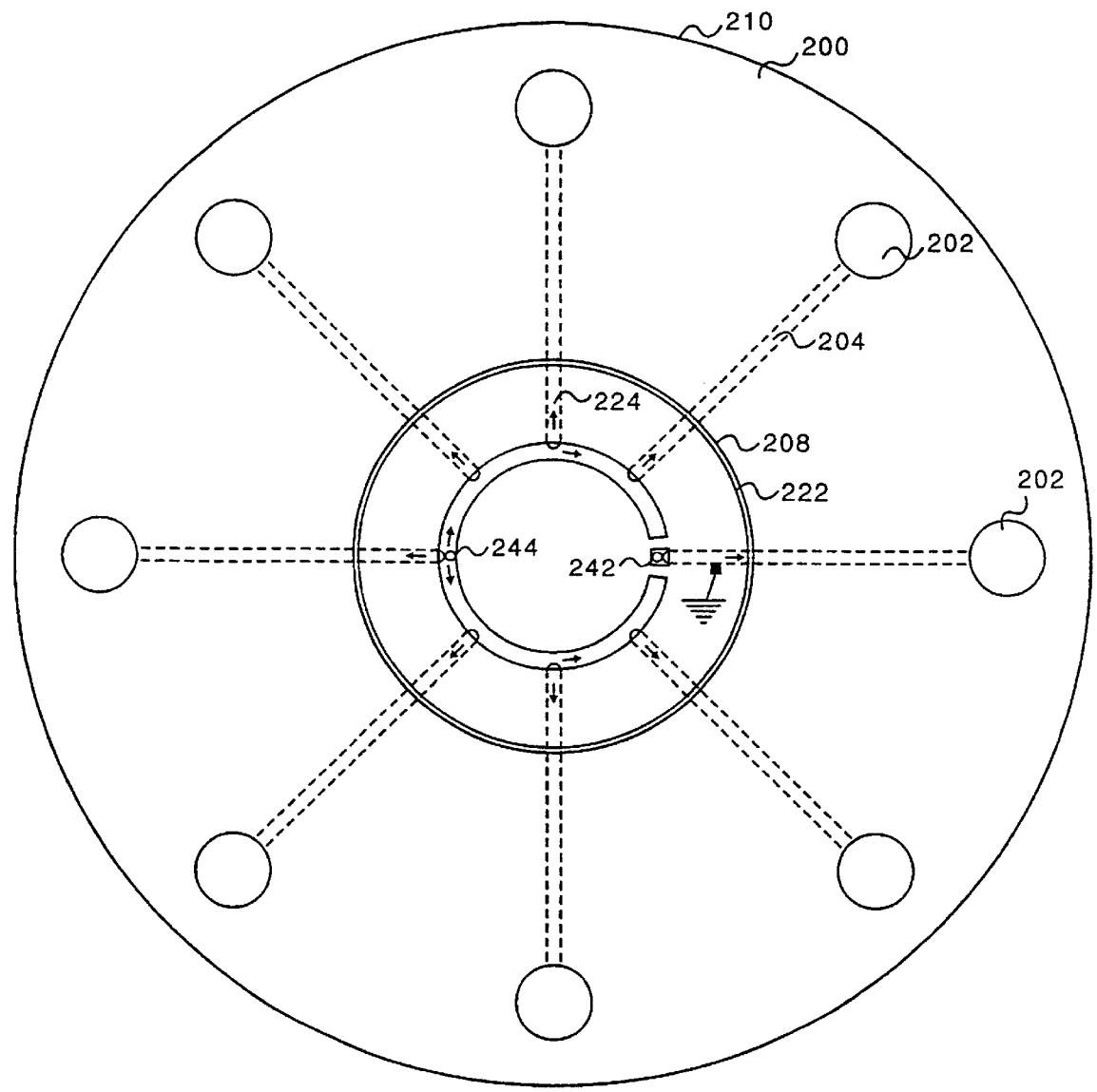
FIG. 16 is a schematic view of a turntable comprising several perfusion chambers, which turntable comprise the rotatable outer part of FIG. 13, the fixed inner part of FIG. 14, and the top part of FIG. 5.

In FIG. 16 the outer part 200, the inner part 220 and the top part 246 have been assembled to constitute the turn table 400. The arrows show the direction of flow for the liquid solutions provided to the turn table 400 through the holes 242 and 244.

By rotating the outer part 200 in relation to the inner part 220, the test perfusion chamber 202' may be moved from it's present position to a new position, and at the same time another perfusion chamber 202 may be moved into the previous position of the test perfusion chamber 202', thereby taking over the function as the test perfusion chamber 202'.

Figure 17:
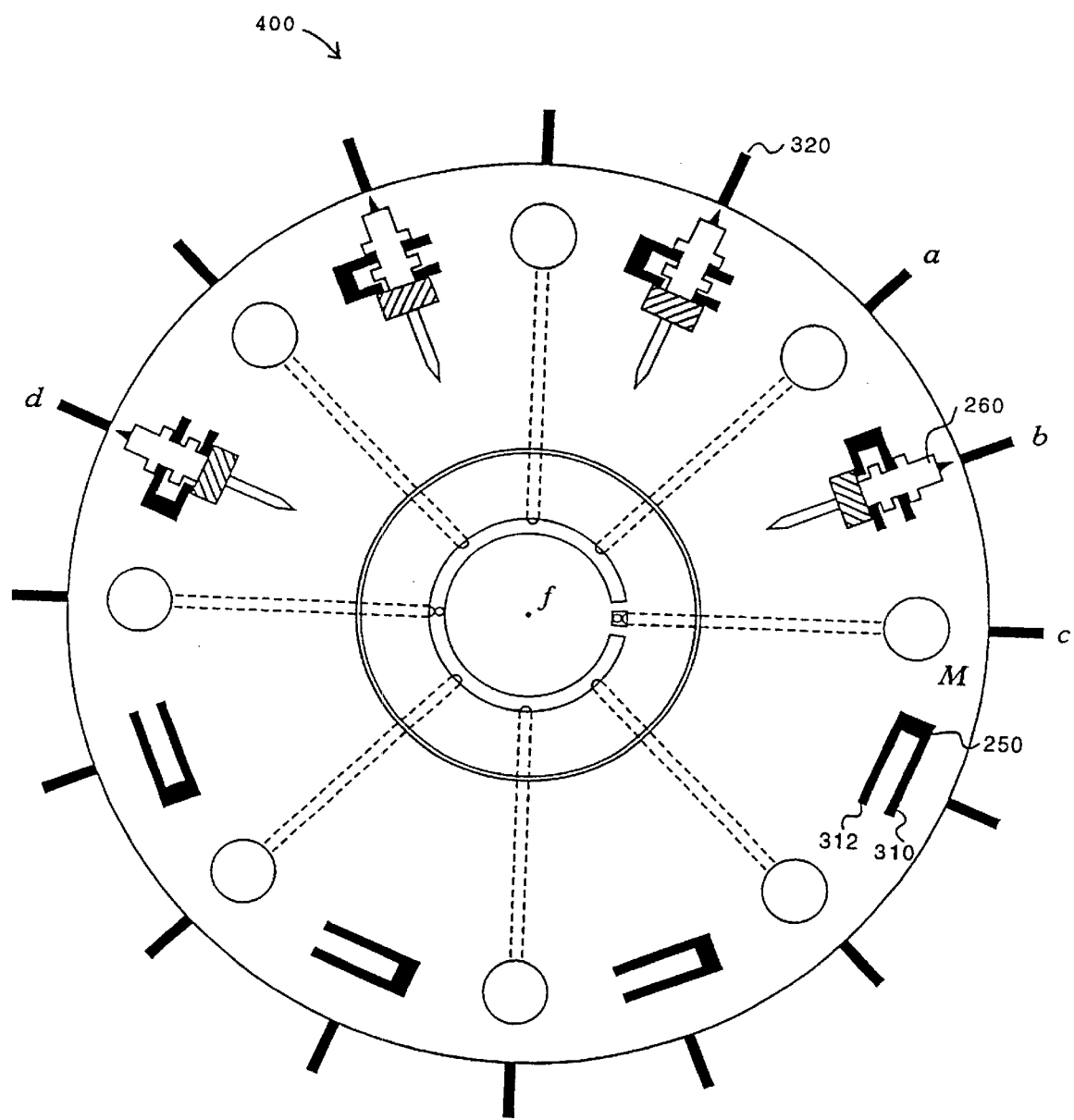
FIG. 17 is a schematic view of the turntable of FIG. 16, further comprising a number of supports each adapted to support a pipette holder.

In FIG. 17 another view of the turn table 400 is displayed. The outer part 200 of the turn table 400 comprises a plurality of pipette holder supports 250, one pipette holder support 250 for each perfusion chamber 202 in the outer part 200. Each of the pipette holder supports 250 is used for holding one pipette holder 260, as shown for half of the pipette holder supports 250.

Figure 18:
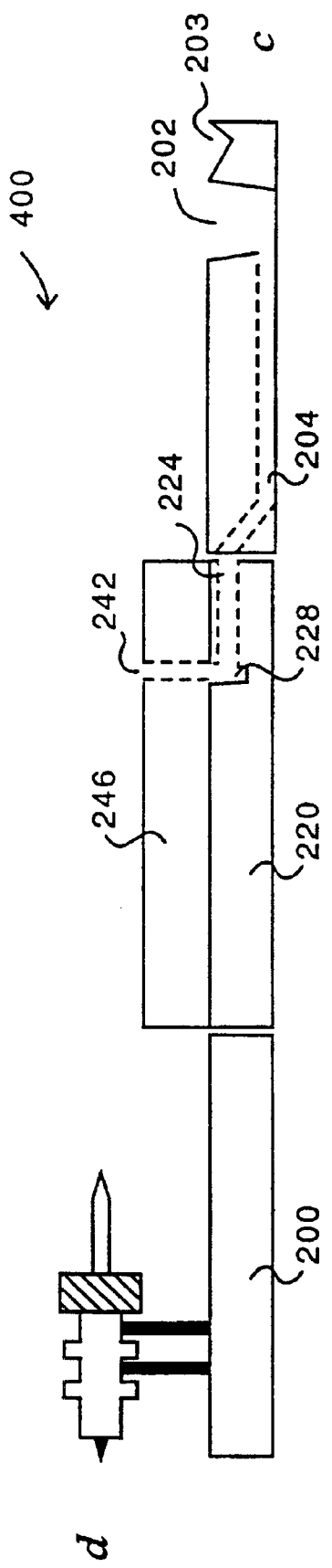
FIG. 18 is a cross-sectional view of the turntable of FIG. 17.

In FIG. 18 a cross section of the turn table 400 is shown. The cross section is seen from the point c at the perimeter of the turn table 400 via the centre f to the point d at the perimeter of the turn table 400. When a liquid solution is supplied to the hole 242 in the top part 246 of the turn table 400, the path comprising the hole 242, the grove 228, the drilled bore 224 and the drilled bore 204 guides the liquid solution from the hole 242 to the perfusion chamber 202. Excessive liquid solution is guided via an overflow grove 203 to a waste chamber (not shown), from where it is removed for disposal through holes (not shown) in the inner part 220 and the top part 246 by a tube connected to a suction pump.

Figure 19:
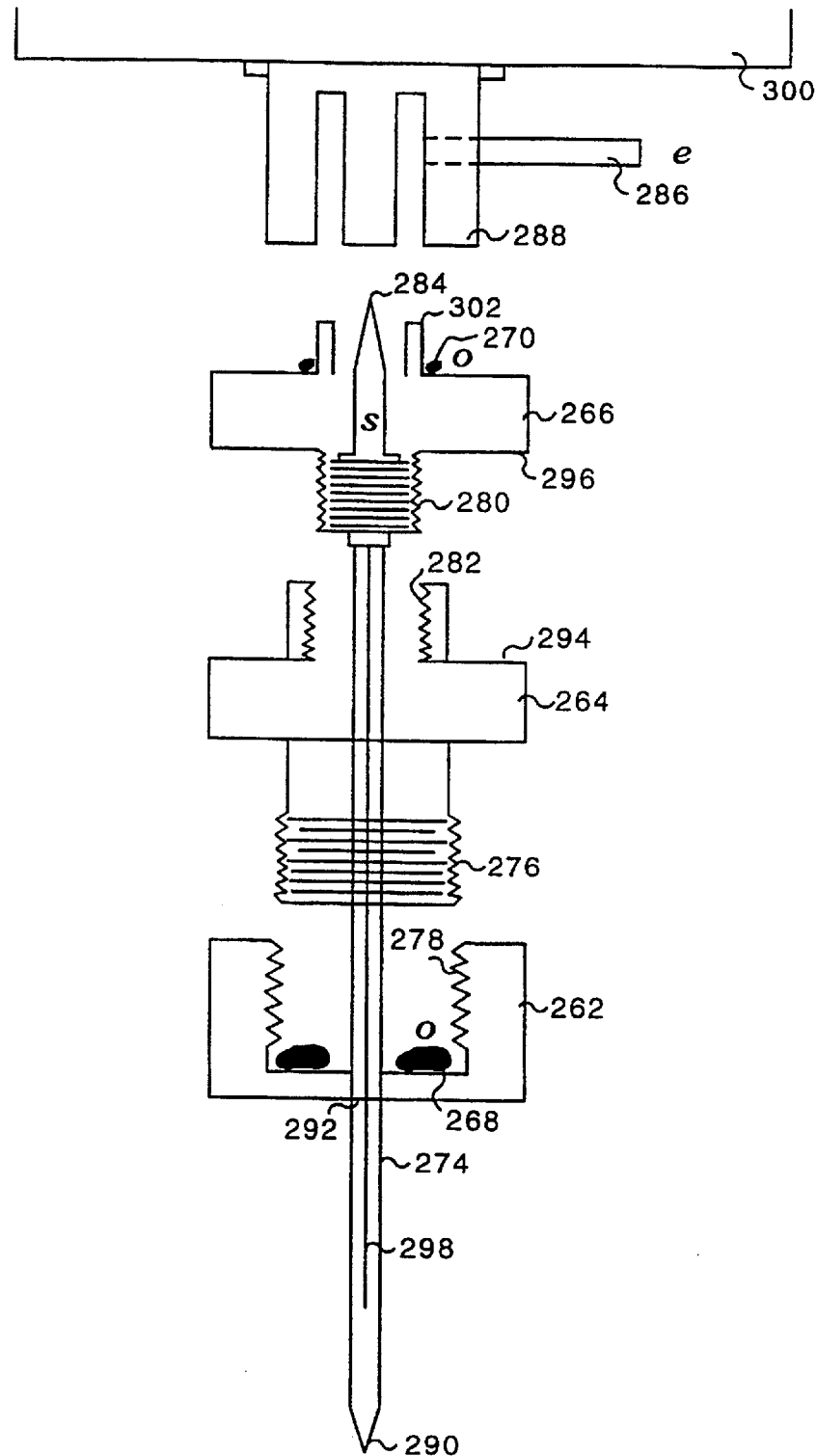
FIG. 19 is a top view of a pipette holder and preamplifier.

In FIG. 19 a detailed view of a pipette holder 260 is displayed. The pipette holder 260 comprises three main parts, the upper part 266, the middle part 264, and the lower part 262. The lower part 262 comprises a first O-ring 268, a hole 292 for a glass pipette 274, and a first thread 278. The middle part 264 comprises a first shoulder 294, a second thread 276 fitting the first thread 278, and a third thread 282. The upper part 266 comprises a second shoulder 296, a fourth thread 280 fitting the third thread 282, a second O-ring 270, and first connecting means 302.

When the pipette holder 260 is assembled, the insertion part 284 is inserted into the upper part 266 from below, and the insertion part 284 is hold in place in the upper part 266 by friction. Soldered to the insertion part 284 is an electrode 298 made from silver and with a layer of silver chloride. The upper part 266 is then connected to the middle part 264 by screwing them together using the threads 280 and 282.

A glass pipe or pipette 274 is inserted into the hole 292 of the lower part 262, and the electrode 298 is inserted into the pipette 274. The lower part 262 is then screwed onto the middle part 264 using the threads 276 and 278. Before tightening the two parts, the glass pipette 274 is pushed up against the lower part of the insertion part 284. When the two parts are screwed tightly together, the first O-ring 268 will seal the opening 292 and fix the glass pipette 274 in it's position.

When the pipette holder 260 with the pipette 274 is to be used for patch clamping, it is mounted on a manipulator 300. The manipulator 300 comprises second connecting means 288 and a terminal 286 connected to a suction pump. The first connecting means 302 of the upper part 266 fits into the second connecting means 288 of the manipulator 300 so that when the first connecting means 302 of the upper part 266 is pushed into the second connecting means 288 of the manipulator 300, it is secured in that position by friction between the first connecting means 302 and the second connection means 288.

The manipulator 300 may also comprise a preamplifier (not shown) for preamplifying the measurement signals obtained during patch clamp.

The second O-ring 270 provides sealing between the manipulator 300 and the upper part 266 of the pipette holder 260. The terminal 286 may be connected to a tube connected to a suction pump. When the pump starts to suck, air or liquid solution will be sucked up through the tiny hole in the tip 290 of the pipette 274.

The advantage of the pipette holder 260 thus provided is that the necessary vacuum that must be applied at the tip 290 of the pipette 274 may be provided by the second connecting means 288 through the pipette holder 260. When changing the pipette 274, the pipette 274 and the pipette holder 260 is discarded, and the pipette holder support 250 is connected to another pipette holder 260 with a new pipette 274. This procedure may, using the provided pipette holder 260, be performed without the otherwise necessary removal of a suction tube mounted on the pipette holder 260 and thereafter mounting the suction tube on a new pipette holder 260, as the suction tube is mounted on the second connecting means 288 to be reused The pipette holder 260 thus provided is ideal for use in an automatic patch clamp apparatus.

When not in use, the pipette holder 260 is mounted on the pipette holder support 250. When the manipulator 300 is moved to pick up the pipette holder 260, the second connecting means 288 is pushed against the first connecting means 302 until a frictional engagement is obtained. The pipette holder support 250 comprises two engaging parts 310 and 312 engaging with the shoulder 296 of the upper part and the shoulder 294 of the middle part 264, so that when the manipulator 300 pushes against the pipette holder 260, the pipette holder 260 is held in place by the engaging parts 310 and 312.

Similarly, when the pipette holder 260 is to be removed from the manipulator 300, the manipulator 300 moves the pipette holder 260 into position in the pipette holder support 250, and when the engaging parts 310 and 312 engages with the shoulders 296 and 294, the first connecting means 302 and the second connecting means 288 may be pulled from each other.

The outer part 200 may be provided with guide pins 320 positioned on the outer perimeter as shown in FIG. 17. When the outer part 200 is to be rotated, the manipulator 300 may push against the guide pins 320, thereby rotate the outer part 200 around it's centre f. The guide pins 320 may also be positioned on top of the outer part 200 between the pipette holder supports 260, or the pipette holder supports 260 may also be used as guide pins, and in both these cases, the manipulator 300 may push against the guide pins or the pipette holder supports 260 and thereby rotate the outer part 200 around it's centre f.

Before using the above described turn table 400, one or more of the pipette holders 260 must be equipped with pipettes and positioned in the pipette holder support 250, and the manipulator 300 should be moved to a neutral or resting position. When measurements is to be started, the manipulator 300 moves to engage with and pick up a pipette holder 260'. The manipulator 300 then moves the pipette holder 260', selected among the plurality of pipette holders 260, to the test perfusion chamber 202' next to the pipette holder 260', where the tip of the pipette is positioned on a chosen cell to be investigated, patch clamp is obtained and the measurement is performed. Positioning of the tip of the pipette on a cell will be described in detail below. When the measurement has been performed, the manipulator 300 moves the pipette holder 260' back to the pipette holder support 250' and the manipulator 300 and the pipette holder 260' are disengaged. The manipulator 300 then pushes against the guide pin 320 to rotate the outer part 200 to a new position, whereafter the manipulator 300 may pick up a new pipette holder 260 to start the procedure again.

The movements of the manipulator 300 may be controlled by a computer, e.g. a standard IBM compatible PC or a computer compatible with an Apple Macintosh (MAC).

When, as described above, the manipulator 300 has moved the tip of the pipette to the test perfusion chamber 202', the tip should be positioned on a suitable cell.

The search for a cell to be patch-clamped and the recognition of the tip of the pipette are based on visual (graphics) information in digital images of the objects (cells and pipette). The digital images may be recorded by an analog video camera connected to a framegrabber, a digital video camera, a digital camera, etc.

The same computer that is used to control the manipulator 300 and used as a basis for the framegrabber and the NeuroPatch software, may also be used for acquiring the measurement data during patch clamp, but a separate computer may also be utilized.

The image that the current implementation of the NeuroPatch software operates on, may be obtained from a standard video camera delivering a PAL S-VHS output signal. This analog signal is digitized in a framegrabber which has been set to display the image in a resolution of 768 by 512 pixels using 24 bits to represent the colour of each pixel (16.7M colour possibilities per pixel=True Colour). While recognition is not being performed, a live image is displayed. Prior to starting the cell and pipette recognition routines, the live image is frozen and a 256 grey level copy of the frozen image is transferred to an image buffer. The recognition routines then operate on the frozen image in the image buffer, but the frozen image will not be changed by the recognition routines. Instead, the results of the recognition routines will be stored in one or more images or image buffers.

Figure 20:
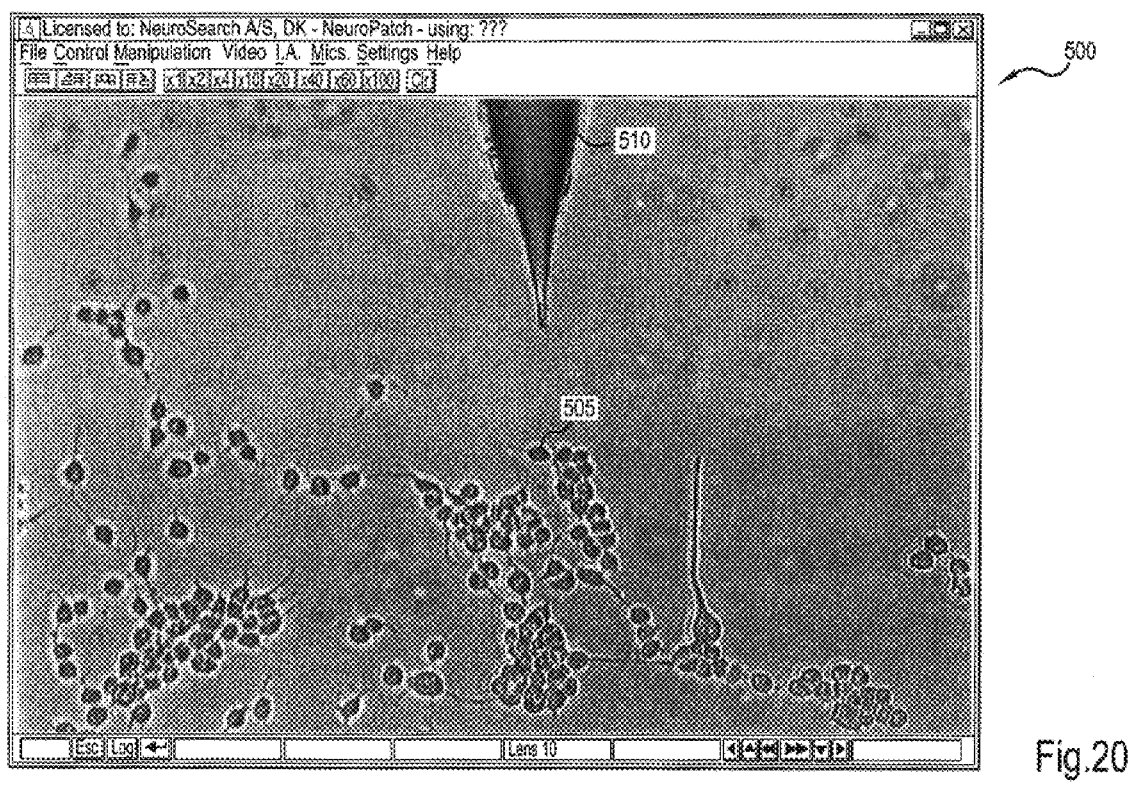
FIG. 20 shows an example of a frozen image of a pipette tip and a number of cells.

An example of a frozen image is shown i FIG. 20. The frozen image 500 comprises a plurality of cells 505 and a pipette 510 with a pipette tip 508.

The selection of a proper cell for patch clamping may be performed by using the following method. The method comprises 5 steps:

1) Normalizing and noise filtering of the image
2) Solidification
3) Size filtering
4) Isolation filtering
5) "Best cell" selection In each of the steps, one or more filters are applied on the image. It should be understood that applying a filter on a digitized first image is performed by applying the filter for each pixel one by one in a first image. The result of the filtering is stored in a second image or image buffer in a position corresponding to the pixel in the first image, and after applying the filter for all pixels in the first image, the second image contains the filtered image This image may then be used for further filtering. A filter may cover more than one pixel in the first image, but the result of the filtering will only be stored in one pixel in the second image. If a pixel in the first image is designated the centre pixel, the eight pixels surrounding the centre pixel may be covered by the filter, and the filter therefore in this case uses 9 pixels in the first image to calculate a new pixel value for a pixel in the second image corresponding to the centre pixel in the first image. A simple example of a filter using 9 pixels, is an averaging or smoothing filter. The average of 9 pixels in a cluster of 3 by 3 pixels in the first image is calculated and stored in the pixel in the position in the second image corresponding to the position of the centre pixel in the first image.

When an image is displayed on a monitor, a specific value of a pixel corresponds to a specific colour (or a specific tone of grey). A value of a pixel may therefore be represented by a colour and vice versa.

In the FIGS. 22–26, filters used in the presently preferred embodiment of the invention is displayed. In each filter, the centre pixel is marked with an "x" and the adjacent or neighbouring pixels used in the filter are marked with a "*". The filter does not necessarily operate on all the adjacent or neighbouring pixels, and the pixels not used are marked with a "–".

When an image has been filtered, the original image or the resulting or filtered image may be displayed on a monitor.

In the following a plurality of user defined parameters are used. These parameters define values to be used when the filters are applied to the image, either for defining parameters of the filters (size, function), or for selecting the pixels in the image to be filtered. In Table 1, the name, range, and default values for the filters are shown.

Step 1

The task of the first step is to convert the 256 grey level image of cells into a binary image comprising pixels having one value of a set of two values. Pixels with a grey level value greater than a calculated threshold value (say lighter pixels) are represented by one value (say the colour white)

and pixels with a grey level value less than the threshold value (say darker pixels) are represented by another value (say the colour red).

While performing the threshold based image conversion, two additional operations are performed at the same time: first, the image is "normalized" in such a way that differences in illumination intensity in different portions of the image will have little influence on whether cells can be recognized or not, and second, "primitive" noise is filtered out of the image.

Figures 21, 22, 23:
FIG. 21 shows 9 pixels blocks of 100 by 100 pixels in a frozen image.
FIG. 22 shows a filter used for spatial filtering in step 1 of the "best cell" determination method.
FIG. 23 shows a "fill" filter used for spatial filtering in step 2 of the "best cell" determination method.

1) First, the average grey level values in 9 pixel blocks of 100 by 100 pixels are calculated, see FIG. 21.
2) Second, based on the average values calculated above, the inter-block average changes per pixel are calculated in both the x- and y-direction.
3) Third, for each of the pixels in the central 600 by 512 pixel region of the image, a combined conversion and filtering is performed:
   a) A grey level threshold value is calculated based on the average values and inter-block average changes per pixel calculated in 1) and 2) above.
   b) A user defined increment value (increment) is added to the threshold value calculated in 3) a) above to form the maximum threshold value for the pixel under investigation.
   c) If the grey level value of the pixel is darker (less) than the maximum threshold value calculated in 3) b) above, the neighbourhood of the pixel is investigated using the filter shown in FIG. 22.

If the number of neighbouring. pixels with a grey level less than or equal to the maximum threshold value is larger than or equal to m (boundsFactor), the pixel is accepted (marked red) else rejected (marked white). The greater m (boundsFactor) is, the greater the collection/clustering of neighbouring pixels must be for the pixel to be accepted.

Step 2

After Step 1, it is possible to see the outlines of the cells and parts of their interiors. The cells should appear as "solid" structures without holes in their interiors. So, in this step an attempt is made to close the holes in the interiors of the cells. The way this is done has the side-effect that small gaps between clusters of cells are also closed. This side-effect later becomes an advantage in the sense that clusters will appear as large structures that will be disqualified due to their size as if it was an artifact.

1) In the central 380 by 380 pixel region of the image (which has been processed in Step 1) a simple "fill" function is applied, see FIG. 23.
   a) If a pixel in the previous step was rejected (unmarked or white) and it's neighbours to the left and to the top were accepted (marked or red) a search is performed.
   b) Moving one pixel to the right at a time it is recorded for how many connected positions the pixels are unmarked (white) while their neighbours to the top are marked (red). The recording stops if more than a user-defined number (horizontalCount) of pixels is counted, if the neighbour to the top is unmarked (white) or if a marked (red) pixel is encountered.
   c) If the stop condition in b) above is different from a marked (red) pixel being encountered, the pixel is ignored. Alternatively, a vertical recording is started in which the number of connected unmarked (white) positions below the pixel is determined. The recording stops if more than a user-defined number (verticalCount) of pixels is counted or if a marked (red) pixel is encountered.
   d) If the stop condition in c) above is different from a marked (red) pixel being encountered, the pixel is ignored. Alternatively, a horizontal "fill" is performed from the base pixel to the found marked (red) pixel in the horizontal direction.

Step 3

After Step 2, it is possible to see filled profiles of various sizes. Cells that are positioned closely to each other may appear as a large block of pixels, while cells that are reasonably isolated will appear at their correct sizes. Now, a size filter is applied so that groups of pixels that are smaller than a minimum size or larger than a maximum size are disqualified from further evaluation.

Figures 24, 25:
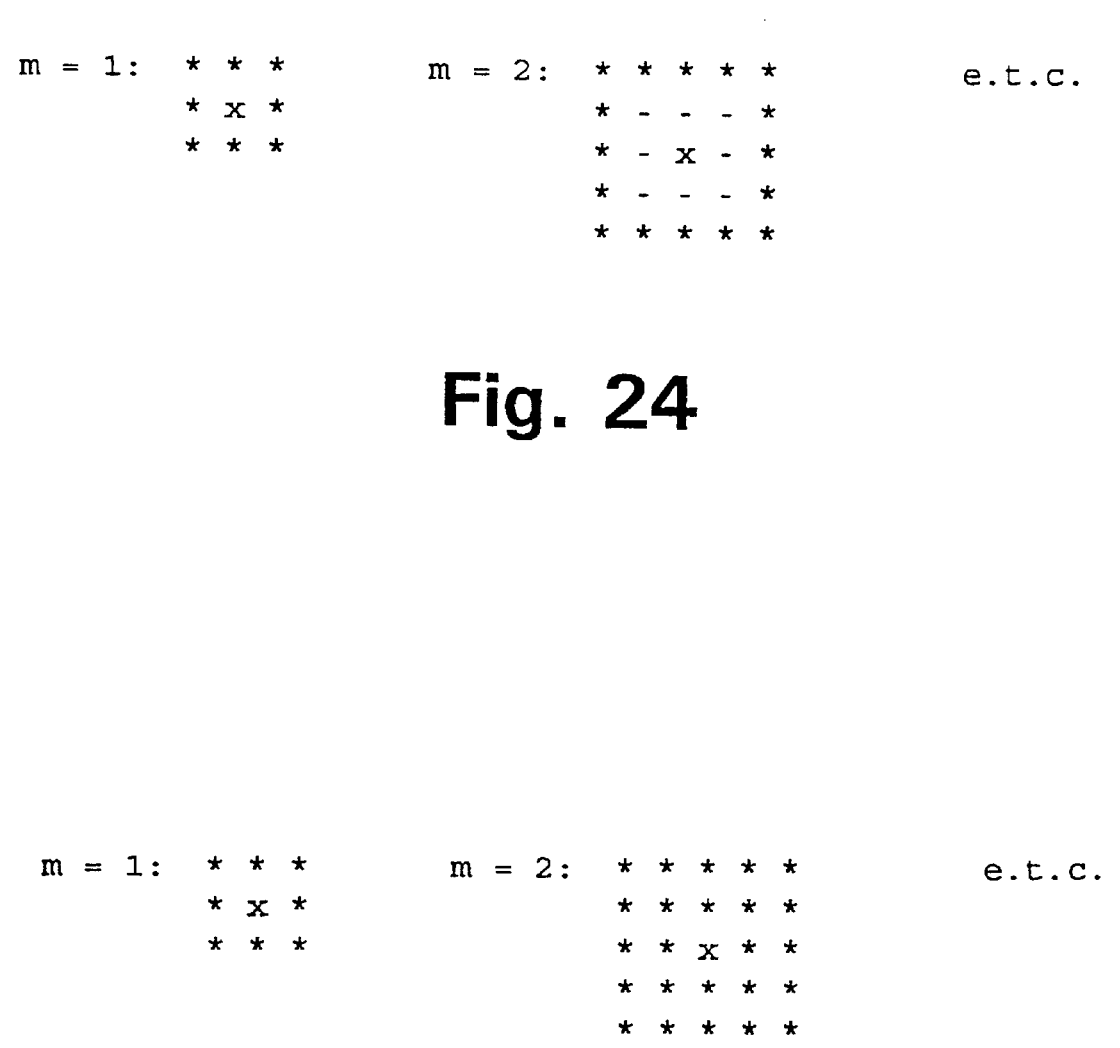

1) In the central 380 by 380 pixel region of the image (which has been processed in step 2) a size filter is applied to each marked (red) pixel, see FIG. 24.
   a) If a pixel is marked (red) the neighbourhood is investigated at a distance of m pixels around it.
   b) For the minimum size check, m is a user-defined low mask value (LowMaskRed). If the number of marked (red) neighbours at distance m from the pixel is less than a user-defined lowpass value (LowPassRed), the pixel under investigation is left unchanged (thereby being disqualified).
   c) Alternatively, the maximum size check is performed. Here, m is a user-defined high mask value (HighMaskRed). If the number of marked (red) neighbours at distance m from the pixel is higher than a user-defined highpass value (HighPassRed), the pixel under investigation is left unchanged (thereby being disqualified). Alternatively, the pixel has passed the size tests and is marked (blue).

Step 4

After Step 3, those clusters of pixels that fulfil the size requirements for being cells are marked (blue). Now, further investigation is made to choose those clusters that have a proper degree of isolation for further evaluation.

1) In the central 360 by 360 pixel region of the image (which has been processed in step 3) an "isolation" filter is applied to each marked (blue) pixel, see FIG. 25.
   a) If a pixel is marked (blue) the neighbourhood is investigated within a distance of m pixels around it. Here, m is a user-defined low mask value (LowMaskBlue).
   b) If the number of marked (blue) pixels within the distance m from the pixel is larger than or equal to a user-defined lowpass value (LowPassBlue) it is investigated up to which value of m (called HighMaskBlue) the neighbourhood as in step 3 still contains marked (blue) pixels. This investigation continues until a value for m is found at which the neighbourhood count is 0 or m is equal to or larger than a user-defined highpass value (HighPassBlue).
   c) If m is larger than or equal to the low mask value plus 1 (LowMaskBlue+1) and m is less than the highpass value. (HighPassBlue), an isolated cluster of marked (blue) pixels has been found. The number of pixels that make up this isolated cluster is counted and a "freeborder" distance is calculated based on a user-defined value (freeBorderBase).
   d) The number of marked (blue) pixels in the "freeborder" band is calculated and if this number is less than the HighMaskBlue value found in b) above, the cluster of marked (blue) pixels is marked (green).

Step 5

After Step 4, those clusters of pixels that are assumed to represent cells suited for patch-clamping are marked (green). Now, further investigation is made to the clusters that represents the "best cells" and to have the coordinates of the centre of gravity of the "best cell" returned.

1) In the central 360 by 360 pixel region of the image (which has been processed in step 4) clusters are marked (green), each representing a possible "best cell". One after the other each cluster of pixels is selected, and the centre of gravidity is found by counting the number of pixels in the x- and y-direction and adding half the x- and y-values to the upper left pixel of the marked cluster.

Hereafter the number of pixels marked green is counted, and the cluster with the largest number of pixels is selected as the "best cell". The function returns with the position of the pixel representing the centre of gravidity.

Another part of the NeuroPatch software relates to recognition of the pipette tip 508 and calculation of the exact position of the pipette tip 508.

When reference is made to the pipette tip 508, it should be understood that because a pipette 510 is formed as a pipe, the pipette tip 508 refers to the centre of the opening of the pipe.

This part of the software may be performed using a method with 5 steps.

1) Mean filtering
2) Normalising and noise filtering the image as well as contrast enhancement by thresholding
3) Determination of a first estimate for the centre line of the tip 508
4) Determination of the optimal approximal position of the pipette 510 on the screen
5) Determination of the geometric centre line of the pipette 610
6) Determination of the tip 508 of the pipette 510

Step 1

The first step in the method is to calculate the average grey level in a part of the image. If the grey level is higher than a predetermined threshold value, the image is considered to be to light, and the pixels in the image is made darker by multiplying the value of each of the pixels with a constant between 0 and 1. This step enhances the contrast in the image in the areas with the image of the tip of the pipette, making a quick and accurate determination of the position of the tip of the pipette possible.

Step 2

The task of the second step is to convert the 256 grey level image into a two-colour image in which pixels with a grey level value greater than a calculated threshold value (say lighter pixels) are represented by one value (say the colour white) and pixels with a grey level value less than the threshold value (say darker pixels) are represented by another value (say the colour red).

While performing the threshold based image conversion, two additional operations are performed at the same time: first, the image is "normalized" in such a way that differences in light conditions in different portions of the image will have little influence on whether the pipette 510 may be recognized or not, and second, "primitive" noise is filtered out of the image.

1) First, the average grey level values in 9 pixel blocks of 100 by 100 pixels are calculated, see FIG. 21.
2) Second, based on the average values calculated above, the inter-block average changes per pixel are calculated in both the x- and y-direction.
3) Third, for each of the pixels in the central 600 by 512 pixel region of the image, the combined conversion and filtering is performed:
   a) A grey level threshold value is calculated based on the average values and inter-block average changes per pixel calculated in 1) and 2) above.
   b) After the determination of the grey level threshold value, each pixel is investigated, and if the grey level of the pixel is less than or equal to 90% of the determined grey level threshold value, the pixel is represented by one value (say the colour red), otherwise the pixel is represented by another value (say the colour white). This means that any pixel in the image is represented by one of two values (red and white). By setting the threshold value distinguishing red and white pixels to 90% of the determined grey level threshold value, the "contrast" of the image is enhanced, and the tip 508 of the pipette 510 is more clearly recognized and the position of the tip 508 easier to determine.

Figure 26:
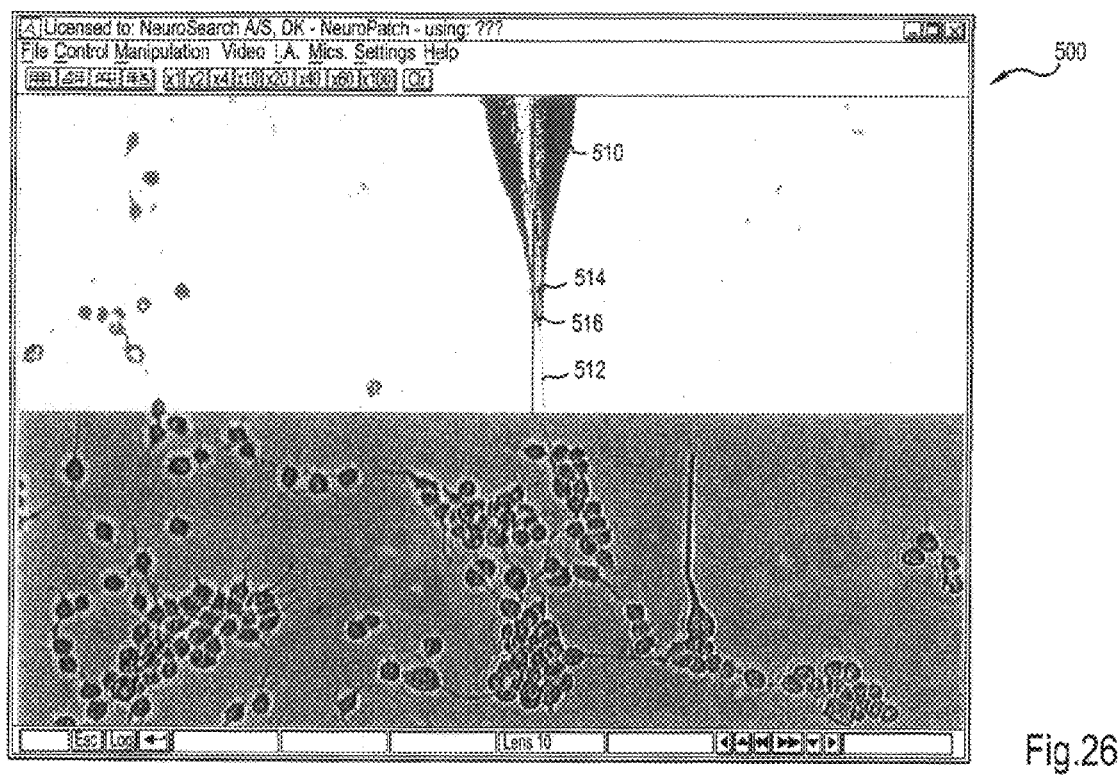
FIG. 26 shows an image of a pipette tip, which position is in the process of being determined.

In FIG. 26 an example of an image that has been filtered according to the above described procedure. Only the upper half of the image has been filtered, and the pipette 510 is clearly detected.

Step 3

After performing the threshold filtering of the image in step 2, a first estimate for the position of the tip 508 of the pipette 510 may be determined. In the image recorded by the camera, the pipette 510 appears as a triangle, and it is normally positioned in such a way that the widest part of the pipette 510 is positioned at the top of the image and the tip 508 of the pipette 510 is positioned approximately at the centre of the image. Therefore it is possible to use the top row of pixels as the start row in the search for the position of the tip 508 of the pipette 510. For each pixel in the top row (x direction) with the value red, the number of pixels below the top pixel in the same column (y direction) with the value red is counted. It is required that the pixels with the value red constitutes a continuous column of red pixels, but as there still may be noise in the image, it is only required that the pixel numbered y and at least one of the pixels numbered y+4, y+7, and y+10 are red, If this is the case, the count (the y value) is incremented, and the pixels below the pixel numbered y is investigated. This procedure is repeated until all the pixels numbered y, y+4, y+7, and y+10 are white, and the previous y-value is stored together with the x-value for that column. This procedure is performed for each x-value in the image, and when finished, it is possible to determine the x-value for the largest y-value. The resulting position (x,y) is the first estimate for a position of the tip 508 of the pipette 510. In FIG. 26 this position is designated 514.

Step 4

The optimal position of the tip 508 of the pipette 510 is in the upper half of the image and in the centre of the image seen in the x-direction. Using the first estimate for the position of the tip 508 of the pipette 510, it is possible to determine if the pipette 510 should be moved, or if the position is acceptable. If the y-coordinate in the first estimate for the position is less than 50 (pixels from the top), the tip 508 is considered too be to close to the top of the image, and the tip 508 should be moved down a distance corresponding to one half of the height of the image. If on the contrary the y-coordinate in the first estimate for the position is larger than 450 (pixels from the top), the tip 508 is considered to be to close to the bottom of the image, and the tip 508 should be moved up a distance corresponding to one half of the height of the image. The tip 508 is moved using the manipulator 300.

Correspondingly, if the x-coordinate in the first estimate for the position is smaller than 158 (pixels) or larger than 610 (pixels) the tip 508 is too close to the sides of the image, and the pipette 510 should be moved towards the centre. The size of the movement is in this case app. one third of the width of the image.

If the pipette 510 is moved in step 4, the steps 1–4 are repeated.

Step 5

After determination of the first estimate of the position of the tip 508 of the pipette 510 and the positioning of the pipette in the desired part of the image, the geometric centre line of the pipette may be determined.

This is done by calculating the average x-coordinate for each row (or y-value) from the top of the image to the y-coordinate of the first estimate using only the pixels with the value red. After calculation of the average coordinates, the best straight line through the determined points may be calculated. This line corresponds to the symmetric line of the pipette 510, and in FIG. 26 this line is designated 512.

Step 6

The last step of the procedure is to calculate the actual position of the tip 508 of the pipette 510. Looking at a line across an ideal pipette tip 508, the pixels should have the values white—red—white—red—white, corresponding to an area outside of and to the left of the pipette 510 (white), the left part of the pipette 510 (red), the area inside the pipette 510 (white), the right part of the pipette 510 (white), and an area outside of and to the right of the pipette 510 (red). The symmetric line of the pipette 510 should be positioned in the white area displaying the centre of the pipette 510.

Starting from the top of the image, it is determined how far down along the symmetric line, the values vary as in the cross section of the ideal pipette 510 (white—red—white—red—white). The investigation is continued along the symmetric line until the width of the middle white part has a width between one and five pixels. The intersection of the symmetric line and last row is determined, and if the values vary as white—red—white—red—white as in the ideal pipette 510, this intersection determines the tip 508 of the pipette 510.

If the values are not white—red—white—red—white, the intersection is determined to be a first estimate of the tip position. The pipette 510 is then moved a bit closer (app. 5–10 µm) to the cells to get the tip 508. in focus of the camera, and steps 1–6 are repeated. If, again, it is not possible to determine the tip 508 position directly, the pipette 510 is moved in the x-y- plane and a second estimate is calculated using steps 1–6. If the first and the second estimates are equal (in this case "equal" means, that the difference between the first and the second estimate should not be larger than 2 pixels in the x- or y-direction) this estimation is used as the tip 508 position, otherwise the pipette is moved again in the x-y plane and the position of the tip determined. This procedure continues until two equal estimates are found.

After completion of the last step, the function returns with a set of coordinates for the detected pipette tip 508. In FIG. 26 this set of coordinates is designated 516.

The NeuroPatch computer program has now determined a position for the "best cell" and a position for the tip 508 of the pipette 510. The manipulator 300 is then controlled to move the tip 508 of the pipette 510 to the centre of the "best cell". When this has been accomplished, suction is applied to the terminal 286, and a giga-seal may be obtained.

TABLE 1

| name: | range: | default: |
|---|---|---|
| increment | 0.5 | 2 |
| boundsFactor | 0.5 | 1 |
| horizontalCount | 0.25 | 15 |
| verticalCount | 0.25 | 15 |
| freeBorderBase | 0.100 | 40 |
| LowMaskRed | 0.3 | 2 |
| LowMaskBlue | 0.3 | 2 |
| LowMaskGreen | 0.3 | 1 |
| HighMaskRed | 0.25 | 10 |
| LowPassRed | 0.25 | 12 |
| LowPassBlue | 0.25 | 20 |
| LowPassGreen | 0.25 | 5 |
| HighPassRed | 0.100 | 60 |
| HighPassBlue | 0.100 | 20 |
| HighPassGreen | 0.100 | 20 |

What is claimed is:

1. An automatic electrode positioning apparatus for connecting an electrode to a cell, comprising:

a chamber for holding cells;

an electrode movably positioned adjacent the chamber;

positioning means for holding and positioning the electrode at desired positions in relation to the chamber, measurement means for determination of an electrical parameter and electrically connected to the electrode and the chamber and forming an electrical circuit comprising the electrode and the chamber;

a controller for controlling the positioning means in response to the parameter determinations so that the electrode can be automatically connected to a selected cell;

selection means for selecting a specific cell to be connected to the electrode, wherein the selection means comprise imaging means for forming an image of cells in the chamber;

digitizing means for recording and digitizing the image by dividing the image into pixels, each of which has a recorded intensity value, the digitizing means being in operating communication with the imaging means; and a memory for storage of the digitized image an electrically connected to the digitizing means.

2. An apparatus according to claim 1, wherein the selection means further comprises user interface means for displaying the image and for user selection of a cell to be connected to the electrode, and a processor that is connected to the memory and that is adapted for determination of the position of the selected cell, and wherein the controller is electrically connected to the selection means and adapted to receive the position of the selected cell and to automatically control the positioning means in response to the received position in such a way that the electrode is positioned at the determined position of the selected cell.

3. An apparatus according to claim 2, wherein the imaging means comprise a video camera.

4. An apparatus according to claim 1, wherein the selection means further comprises a processor that is connected to the memory and that is adapted for processing the digitized image for identification of cells in the chamber, selection of one cell to be connected to the electrode, and determination of the position of the selected cell in the chamber, and wherein the controller is electrically connected to the selection means and adapted to receive the position of the selected cell and to automatically control the positioning means in response to the received position in such a way that the electrode is positioned at the determined position of the selected cell.

5. An apparatus according to claim 4, wherein the imaging means comprise a video camera.

6. An apparatus according claim 1, further comprising a pipette comprising the electrode and having a pipette tip adapted to provide a high electrical resistance seal with the surface of a cell membrane, wherein the positioning means are adapted for holding and positioning the pipette at desired positions in relation to the chamber, and the controller is adapted for automatically controlling the positioning means in response to the received position in such a way that the pipette tip is positioned at the determined position of the selected cell and provides a high electrical resistance seal with the cell membrane of the selected cell whereby an electrical parameter of the cell membrane can be determined without intervention of a human operator.

7. An apparatus according to claim 6, wherein the processor is further adapted for processing a digitized image for identification of the pipette tip, and determination of the position of the pipette tip.

8. An apparatus according to claim 7, wherein the imaging means comprise a video camera.

9. An apparatus according to claim 6, wherein the imaging means comprise a video camera.

10. An apparatus according to any of claims 1–2, 4 or 6–7, wherein the digitizing means comprise a video camera.

11. An apparatus according to any of claims 1–2, 4 or 6–7, wherein the processor is adapted to identify pixels onto which a cell is imaged utilizing spatial filtering of the image.

12. An apparatus according to claim 11, wherein the spatial filtering comprises identifying and marking with a first mark a pixel as a pixel onto which a cell has been imaged if the pixel values of a specific number of neighbouring pixels to the pixel in question, including the pixel in question, are lower than a first threshold value.

13. An apparatus according to claim 12, wherein the spatial filtering further comprises identifying and marking with a second mark a group of neighbouring pixels marked with the first mark onto which a single cell is imaged by determining the number of pixels comprised in the group of neighbouring pixels and marking groups having a number of pixels within a predetermined range.

14. An apparatus according to claim 13, wherein the spatial filtering further comprises identifying and marking with a third mark a group of neighbouring pixels marked with the second mark if the distance from pixels of the group of neighbouring pixels to pixels marked with the first mark is greater than a predetermined minimum distance.

15. An apparatus according to claim 14, wherein the selected cell is selected among cells that are imaged onto corresponding groups of neighbouring pixels marked with the third mark.

16. An apparatus according to claim 15, wherein the position of the centre pixel of the selected cell constitutes the determined position of the selected cell.

17. An apparatus according to any of claims 2, 4 or 6–7, wherein the processor is adapted to identify pixels onto which the pipette tip is imaged utilizing a spatial filtering of the image.

18. An apparatus according to claim 17, wherein the spatial filtering further comprises identifying and marking with a fourth mark a pixel as a pixel onto which the pipette tip is imaged when the pixel values of a specific number of neighbouring pixels to the pixel in question, including the pixel in question, are lower than a second threshold value.

19. An apparatus according to claim 18, wherein the spatial filtering further comprises identifying a line of pixels, each pixel of the line being positioned at the centre of pixels marked with the fourth mark and being positioned in the row of the pixel in question.

20. An apparatus according to claim 19, wherein the position of the pipette tip is determined as the position of an end pixel of the line.

21. An apparatus according to claim 1 further comprising:

a chamber member having a plurality of chambers for holding cells;

chamber member moving means for sequentially moving the chambers from a chamber storage position to an operating position;

wherein the chamber member further comprises adapters for holding pipettes, the positioning means being further adapted to selectively withdraw a pipette from its adapter and to insert the pipette into its adapter when the corresponding chamber is in its operating position.

22. An apparatus according to claim 21, further comprising means for supplying liquid to the chambers of the chamber member.

23. An apparatus according to claim 22, wherein the means for supplying liquid to the chambers of the chamber member comprises means for supplying a first liquid to the chambers in a storage position and a second liquid to the chamber in the operating position.

24. An apparatus according to any of claims 21–23, further comprising suction means for removing excess liquid flowing through the chambers.

25. An apparatus according to any of claims 21–23, wherein the chamber member is a turn-table rotatable positioned in the apparatus and having wells therein defining the chambers.

26. An apparatus according to claim 1, further comprising a pipette comprising the electrode and having a pipette tip adapted to provide a high electrical resistance seal with the surface of a cell membrane;

wherein the positioning means are adapted for holding and positioning the pipette at desired positions in relation to the chamber, and the controller is adapted for automatically controlling the positioning means in response to the received position in such a way that the pipette tip is positioned at the determined position of the selected cell and provides a high electrical resistance seal with the cell membrane of the selected cell whereby an electrical parameter of the cell membrane can be determined without intervention of a human operator.

27. An apparatus according to claim 1, wherein the imaging means comprise a video camera.

28. A method for automatically connecting an electrode to a cell, comprising the steps of:

positioning a chamber for holding cells in an operating position in which connection of the electrode to the cell may be performed;

positioning the electrode adjacent the chamber in its operating position;

determining an electrical parameter in an electrical circuit comprising the electrode and the chamber;

controlling the positioning of the electrode in relation to the chamber in response to the parameter determinations so that the electrode can be automatically connected to a selected cell;

selecting a specific cell to be connected to the electrode;

forming and image of cells in the chamber;

recording and digitizing the image by dividing the image into pixels, each of which has a recorded intensity value; and storing the digitized image in a memory.

29. A method according to claim 28, further comprising the steps of displaying the image, user selection of a cell to be connected to the electrode, automatically determining the position of the selected cell, automatically positioning the electrode at the determined position of the selected cell.

30. A method according to claim 28, further comprising the steps of automatically identifying cells in the chamber, selecting one cell to be connected to the electrode, and determining the position of the selected cell in the chamber, and automatically positioning the electrode at the determined position of the selected cell.

31. A method according to claim 30, wherein the step of identifying cells comprises the step of spatially filtering the image for identification of pixels onto which a cell has been imaged.

32. A method according to claim 31, wherein the step of spatial filtering comprises the step of marking with a first mark a pixel as a pixel onto which a cell has been imaged if the pixel values of a specific number of neighbouring pixels to the pixel in question, including the pixel in question, are lower than a threshold value.

33. A method according to claim 32, wherein the step of spatial filtering further comprises the step of marking with a second mark a group of neighbouring pixels marked with the first mark onto which a single cell is imaged by determining the number of pixels comprised in the group of neighbouring pixels and marking groups having a number of pixels within a predetermined range.

34. A method according to claim 33, wherein the step of spatial filtering further comprises the step of marking with a third mark a group of neighbouring pixels marked with the second mark if the distance from pixels of the group of neighbouring pixels to pixels marked with the first mark is greater than a predetermined minimum distance.

35. A method according to claim 34, wherein the step of selecting a cell comprises selection of a cell among cells that are imaged onto corresponding groups of neighbouring pixels marked with the third mark.

36. A method according to claim 28, wherein the electrode is contained in a pipette having a pipette tip that is adapted to provide a high electrical resistance seal with the surface of a cell membrane, and wherein the step of connecting comprises automatically controlling the positioning of the pipette in such a way that the pipette tip is positioned at the determined position of the selected cell and provides a high electrical resistance seal with the cell membrane of the selected cell whereby an electrical parameter of the cell membrane can be determined without intervention of a human operator.

37. A method according to claim 36, further comprising the step of processing a digitized image for identification of the pipette tip, and determination of the position of the pipette tip.

38. A method according to any of claims 36–37, wherein the position of the centre pixel of the selected cell constitutes the determined position of the selected cell.

39. A method according to any of claims 36–37, further comprising the step of identifying pixels onto which the pipette tip is imaged utilizing spatial filtering of the image.

40. A method according to claim 39, further comprising the step of identifying and marking with a fourth mark a pixel as a pixel onto which the pipette tip is imaged when the pixel values of a specific number of neighbouring pixels to the pixel in question, including the pixel in question, are lower than a second threshold value.

41. A method according to claim 40, further comprising the step of identifying a column of pixels, each pixel of the column being positioned at the centre of pixels marked with the fourth mark and being positioned in the row of the pixel in question.

42. A method according to claim 41, further comprising the step of determining the tip of the pipette as the position of an end pixel of the column.

43. A method according to any of claims 28–30 or 36–37, further comprising the steps of arranging a plurality of chambers for holding cells in a chamber member, sequentially moving each of the chambers from a chamber storage position to the operating position.

44. A method according to claim 43, further comprising the steps of arranging adapters for holding pipettes on the chamber member, each adapter being positioned adjacent a corresponding chamber.

45. A method according to claim 43, further comprising the step of supplying liquid to the chambers of the chamber member.

46. A method according to claim 45, wherein the step of supplying liquid to the chambers of the chamber member comprises the steps of supplying a first liquid to the chambers in a storage position and a second liquid to the chamber in the operating position.

47. A method according to claim 43, further comprising the step of removing excess liquid flowing through the chambers.

* * * * *